United States Patent [19]

Revel et al.

[11] Patent Number: 5,071,963
[45] Date of Patent: Dec. 10, 1991

[54] INTERFERON-INDUCED HUMAN (2'-5') OLIGO A SYNTHETASE

[75] Inventors: Michel Revel; Judith Chebath, both of Rehovot, Israel

[73] Assignee: Yeda Research and Developement Co., Ltd., Rehovot, Israel

[21] Appl. No.: 36,104

[22] Filed: Apr. 8, 1987

Related U.S. Application Data

[63] Continuation-in-part of Ser. No. 833,212, Feb. 25, 1986, which is a continuation-in-part of Ser. No. 601,782, Apr. 18, 1984, abandoned.

[30] Foreign Application Priority Data

Aug. 26, 1985 [IL] Israel .................................. 76233
Apr. 8, 1986 [IL] Israel .................................. 78445

[51] Int. Cl.$^5$ ................... A61K 37/04; G01N 33/532
[52] U.S. Cl. .................................... 530/387; 435/6; 435/7.1; 435/7.4; 435/6.9; 435/91; 435/810; 436/501; 436/504; 436/86; 436/800; 436/804; 436/813; 424/85.8; 935/110

[58] Field of Search .................... 435/6, 810, 7.1, 7.4, 435/7.9, 91; 436/501, 504, 86, 800, 804, 813; 530/387; 424/85.8; 935/110

[56] References Cited

PUBLICATIONS

Shimizu et al. (1983) J. of Biochemistry, vol. 94, No. 5, pp. 1421–1428.

*Primary Examiner*—Robert A. Wax
*Assistant Examiner*—Ardin H. Marschel
*Attorney, Agent, or Firm*—John P. White

[57] ABSTRACT

Human DNA encoding enzymes having (2'-5') oligo A synthetase has been sequenced. The amino acid sequences of the enzymes have been deduced. Antigenic peptides have been prepared and have been used to raise antibodies which recognize and immunoprecipitate the 40 kd, 46 kd, 67 kd and 100 kd forms of (2'-5') oligo A synthetase. Methods of monitoring interferon activity in a subject are presented.

8 Claims, 33 Drawing Sheets

Figure 1(b)

```
                                         30                                      60
TTT CGG GTC TTG GAA TTA GTC ATA AAC TAC CAG CAA CTC TGC ATC TAC TGG ACA AAG
PHE ARG VAL LEU GLU LEU VAL ILE ASN TYR GLN GLN LEU CYS ILE TYR TRP THR LYS
                                         90                                     120
TAT TAT GAC TTT AAA AAC CCC ATT ATT GAA AAG TAC CTG AGA CAG CTC ACG AAA CCC
TYR TYR ASP PHE LYS ASN PRO ILE ILE GLU LYS TYR LEU ARG GLN LEU THR LYS PRO
         Sau3a1                         150                                    180
AGG CCT GTG ATC CTG GAC CCG GCG CCT ACA GGA AAC TTG GGT GGA GAC CCA AAG
ARG PRO VAL ILE LEU ASP PRO ALA PRO THR GLY ASN LEU GLY GLY ASP PRO LYS
                                        210                                    240
GGT TGG AGG CAG CTG GCA CAA GAG GCT GAG CTG TGG AAT TAC TGC TTT AAG AAT
GLY TRP ARG GLN LEU ALA GLN GLU ALA GLU LEU TRP ASN TYR CYS PHE LYS ASN
                                        270                                    300
TGG GAT GGG TCC CCA GTG AGC TCC TGG ATT CTG CTG GTG CCT AGA CCT GCT CTG
TRP ASP GLY SER PRO VAL SER SER TRP ILE LEU LEU VAL ARG PRO ALA SER LEU
                                        330                                    360
CCA TTC ATC CCT GCC CCT CTC CAT GAA GCT TGA GAC ATA TAG ACC ATT CTT TCC
PRO PHE ILE PRO ALA PRO LEU HIS GLU ALA
                                        390                                    420
AAA GAA CTT ACC TCT TGC CAA AGG CCA TTT ATA TTC ATA TAG TGA CAG GCT GTG CTC CAT
                                        450                                    480
ATT TTA CAG TCA TTT TGG TCA CAA TCG AGG GTT TCT GGA ATT TTC ACA TCC CTT GTC CAG
EcoR1                                   510
AAT TCA TTC CCC TAA GAG TAA TAA TAA ATA ATC TCT AAC ACC AAA
```

Figure 2
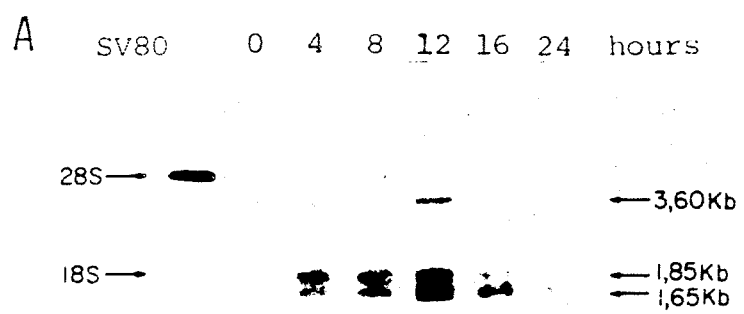
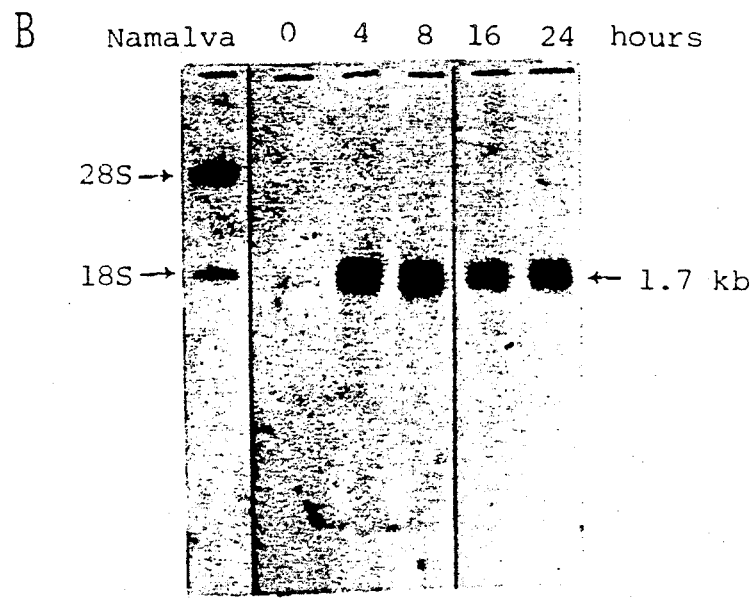

Figure 4(b)

```
                                         30                                    60
TTA|ACA AGG GAT AAA AGT ATC AAT TCT TTG AAG AAA TTG GTT TTA AGG AAA CTT CGG AGA
   THR ARG ASP LYS SER ILE ASN SER LEU LYS LYS LEU VAL LEU ARG LYS LEU ARG ARG 90                                   120
AAG GCA TTA GAT CTG GAA AGC TTG AGC CTC CTT GGG TTC GTC TAC AAA TTB GAA GGA AAT
LYS ALA LEU ASP LEU GLU SER LEU SER LEU LEU GLY PHE VAL TYR LYS LEU GLU GLY ASN 150                                   180
ATG AAT GAA GCC CTG GAG TAC TAT GAG CGG GCC CTG AGA CTG GCT GCT GAC TTT GAG AAC
MET ASN GLU ALA LEU GLU TYR TYR GLU ARG ALA LEU ARG LEU ALA ALA ASP PHE GLU ASN 210                                   240
TCT GTG ABA CAA GGT CCT TAG GCA CCC AGA TAT CAG CCA CTT TCA CAT TTC ATT ICA TTT
SER VAL ARG GLN GLY PRO END 270                                   300
TAT GCT AAC ATT TAC TAA TCA TCT TTT CTG CTT ACT GTT TTC AGA AAC ATT ATA ATT CAC

330
TGT AAT GAT GTA ATT CTT GAA TAA TAA ATC TGA CAA AAT ATT (A)λ
```

Figure 7(a₁)

|   |   |
|---|---|
| a₁ | a₂ |
| a₃ | a₄ |

```
     1                                           30       (1)         Sau3a
16. GAG GCA GTT CTG TTG CCA CTC TCT CTC TCA ATG ATG GAT CTC AGA AAT ACC CCA
    GLU ALA VAL LEU LEU PRO LEU SER LEU SER MET MET ASP LEU ARG ASN THR PRO
    91                                          120      (31)
                        Sph1
16  CTC TTG CCA GAC ACG TGT TTC CGC ATG CAA ATC GAC CAT GCC ATT GAC ATC TGT
    LEU LEU PRO ASP THR CYS PHE ARG MET GLN ILE ASP HIS ALA ILE ASP ILE CYS
    181                       exon 3            210      (61)      exon 4
16  TCC TAC CCT GTG TGT GTG TCC AAG GTG TTA GGT GGC TCC AAG GGC
    SER TYR PRO VAL CYS VAL SER LYS VAL VAL GLY LYS GLY SER SER GLY LYS THR*
    271                                          300      (91)
16  GTC TTC CTC ACT CCT CTC ACC ACT TTT CAG GAT CAG TTA AAT CGC CGG GAG TTC
    VAL PHE LEU SER PRO LEU THR THR PHE GLN ASP GLN LEU ASN ARG ARG GLU PHE
    361                                          390      (121)
16  CAA AGA GAG GCA CTT TCC AAG GTG TTT GAG GTC CAG GCT CCA CGC TGG GGC AAC
    GLN ARG GLU ALA LEU SER LYS VAL PHE GLU VAL GLN ALA PRO ARG TRP GLY ASN
    451                                          480      (151)     exon 4|exon 5
16  CAG CTC GGG GAG GTG GTG GAG TTC GAT CTC CCT GCC TTT GAT GCC CTG GGT CAG
    GLN LEU GLY GLU VAL VAL GLU PHE ASP LEU PRO ALA PHE ASP ALA LEU GLY GLN
    541                                          570      (181)
                                                         Pst 1
16  TAT GTC AAG CTC ATC GAG GAG TGC ACC CTG CAG AAA CTG GGC GAG TTC TCC ACC
    TYR VAL LYS LEU ILE GLU GLU CYS THR LEU GLN LYS LEU GLY GLU PHE SER THR
    631                                          660      (211)
                                                         Kpn1   exon 5
16  C   CGC CCC ACC AAG CTC AAG AGC CTA ATC GTC AAG CAC TGG TAC CAA AAT
    GLN ARG PRO THR LYS LEU LYS SER LEU ILE ARG LEU VAL LYS HIS TRP TYR GLN ASN
```

Figure 7(a₂)

| a₁ | a₂ |
|----|----|
| a₃ | a₄ |

```
 60                                                              90
GCC AAA TCT CTG GAC AAG TTC ATT GAA GAC TAT
ALA LYS SER LEU ASP LYS PHE ILE GLU ASP TYR
150                                                             180
GGG TTC CTG AAG CTG AAA GAA ACG TGC TTC CGA GGT AGC
GLY PHE LEU LYS LEU LYS GLU THR CYS PHE ARG GLY SER
                            Sau3a
240                                                             270
ACC CTC AGA GGC CGA TCT GAC GCT CTG
THR LEU ARG GLY ARG SER ASP ALA LEU
                                      Pvu2
330                                                             360
                                          GAC GTT
                                          LEU VAL
ATC CAG GAA ATT AGG AGA CAG CTG GAA GCC TGT
ILE GLN GLU ILE ARG ARG GLN LEU GLU ALA CYS
420                                                             450
CCC CGT GCG CTC AGC TTC GTA CTG ACT TCG CTC
PRO ARG ALA LEU SER PHE VAL LEU SER SER LEU
510                                                             540
TTG ACT GGC AGC TAT AAA CCT AAC CCC CAA ATC
LEU THR GLY SER TYR LYS PRO ASN PRO GLN ILE
600                                                             630
TGC TTC ACA GAA CTA CAG AGA GAC TTC CTG AAG
CYS PHE THR GLU LEU GLN ARG ASP PHE LEU LYS
690 exon 6 Hind 3                                               720
TGT AAG AAG CTT GGG AAG CTG CCA CCT CAG
CYS LYS LYS LEU GLY LYS LEU PRO PRO GLN
```

Figure 7(a₃)

|     |     |
| --- | --- |
| a₁  | a₂  |
| a₃  | a₄  |

```
                 SacI                                              750  (241)
721
  6 TAT GCC CTG GAG CTC CTG ACG GTC TAT GCT TGG GAG CGA GGG AGC ATG AAA
    TYR ALA LEU GLU LEU LEU THR VAL TYR ALA TRP GLU ARG GLY SER MET LYS
811                                                                840
    GAA TTA GTC ATA AAC TAC CAG CAA CTC TCC ATC TAC TGG ACA AAG TAT TAT
    GLU LEU VAL ILE ASN TYR GLN GLN LEU SER ILE TYR TRP THR LYS TYR TYR
                      exon 6 | exon 7                             (271)
901                         Sau3a 930                              (301)
    CAG CTC ACG AAA CCC AGG CCT GTG ATC CTG GAC CCG GCG GAC CCT ACA GGA
    GLN LEU THR LYS PRO ARG PRO VAL ILE LEU ASP PRO ALA ASP PRO THR GLY
991                                       1020                     (331)
    GCA CAA GAG GCT GAG GCC TGG CTG AAT TAC CCA TGC TTT AAG AAT TGG GAT
    ALA GLN GLU ALA GLU ALA TRP LEU ASN TYR PRO CYS PHE LYS ASN TRP ASP
1081                                        1110   Hind3
    CCT GCT TCC TCC CTG CCA TTC ATC CCT GCC CCT CTC CAT GAA GCT TGA GAC
    PRO ALA SER SER LEU PRO PHE ILE PRO ALA PRO LEU HIS GLU ALA END
1171                                       1200                    (361)
    TGC CAA AGG CCA TTT ATA TTC ATA TAG TGA CAG GCT GTG CTC CAT ATT TTA
                   EcoRl-Xmn1          1290
1261
    ACA TCC CTT GTC CAG AAT TCA TTC CCC TAA GAG TAA TAA ATA ATC TCT
```

Figure 7(a₄)

|a₁|a₂|
|a₃|a₄|

```
                                      780                                               810
ACA CAT TTC AAC ACA GCC CAA GGA TTT CGG ACG GTC TTG
THR HIS PHE ASN THR ALA GLN GLY PHE ARG THR VAL LEU
 Aha3                              870                                                  900
GAC TTT AAA AAC CCC ATT ATT GAA AAG TAC CTG AGA AGG
ASP PHE LYS ASN PRO ILE ILE GLU LYS TYR LEU ARG ARG
                 960                                   Pvu2                 990
AAC TTG GGT GCA GAC CCA AAG GGT TGG AGG CAG CTG
ASN LEU GLY GLY ASP PRO LYS GLY TRP ARG GLN LEU
         1050  Sac1                                                1080
GGG TCC CCA GTG AGC TCC ATT CTG CTG CTG AGA CCT
GLY SER PRO VAL SER SER ILE LEU LEU VAL ARG PRO
         1140                                                      1170
ATA TAG CTG GAG ACC ATT CTT TCC AAA GAA CTT ACC TCT
         1230                                                      1260
CAG TCA TTT TGG TCA CAA TCG AGG GTT TCT GGA ATT TTC
         1320                                                      1350
AAC ACCAAAAA...
```

```
                    exon 6 | exon 7a  Sau3a  930          (301)
901  CAG CTC ACG AAA CCC AGG CCT GTG ATC CTG GAC CCG GCG GAC CCT ACA
     GLN LEU THR LYS PRO ARG PRO VAL ILE LEU ASP PRO ALA ASP PRO THR
                                      1020                  (331)
991  GCA CAA GAG GCT GAG GCC TGG CTG AAT TAC CCA AAT TGC TTT AAG AAT TGG
     ALA GLN GLU ALA GLU ALA TRP LEU ASN TYR PRO ASN CYS PHE LYS ASN TRP
     1081 (glycos.)          Sau3a 1110        (361)
     AAC AGT ACA GAC GAT GAG ACC GAC GAT CCC AGG ACG TAT CAG AAA TAT
     ASN SER THR ASP ASP GLU THR ASP ASP PRO ARG THR TYR GLN LYS TYR
1171                              1200                     (391)
8 CCC AGC ACG CTC CAG GCA TCC ACC CCA CAG GCA GAA CAG GAG GAC TGG
  PRO SER THR LEU GLN ALA SER THR PRO GLN ALA GLU GLN GLU ASP TRP
1261                              1290
8 GGC TCC AGT GTT ATC TGG ACC AGT TCC TTC ATT TTC AGG TGG GAC TCT
1351                              1380
8 TCC AAG ACA GAA CCC AAG TCT CCT GAC TCC TGG CCT TCT ATG CCC TCT
1441   Xmn1                       1470
8 ACC TAT TCT CTG AAA ATA TTC CCT GAG AGA GAA CAG AGA GAT TTA GAT
1531                              1560
8 ATG GGA GGG TAA TGT CTA ATG TAT TAT CAA TAA CAA TAA AAA TAA AGC
```

```
                                                  Pvu2  990
GGA AAC TTG GGT GGT GGA GCA CCA AAG GGT TGG AGG CAG CTG
GLY ASN LEU GLY GLY GLY ALA PRO LYS GLY TRP ARG GLN LEU
       960
                                       exon 7a |exon 8 1080
         1050    Sac1
GAT GGG TCC CCA GTG AGC TCC TGG ATT CTG CTG|GCT GAA AGC
ASP GLY SER PRO VAL SER SER TRP ILE LEU LEU ALA GLU SER
                                                     1170
GGT TAC ATT GGA ACA CAT GAG TAC CCT CAT TTC TCT CAT AGA
GLY TYR ILE GLY THR HIS GLU TYR PRO HIS PHE SER HIS ARG
        1140                                         1260
ACC TGC ACC ATC CTC TGA ATG CCA GTG CAT CTT GGG GGA AAG
THR CYS THR ILE LEU END
Sau3a   1230                                         1350
TGA TCC AGA GAA GAC AAA GCT CCT CAG TGA GCT GGT GTA TAA
        1320                                         1440
ATC CTA TAG ATA ACA TTC TCC AGA GCC TCA CTT CAT TCC
        1410                                     1530
AAG AGA ATG AAA TTC CAG CCT TGA CTT TCT TCT GTG CAC CTG
        1500
AAA TAC CAAAAA...
```

Figure 11

```
                         -80           -70           -60           -50           -40
       Sau 3a
E      AAGATCCTGT    CTCCAAAAAA    TAATAAAATA    AAATAAAAAT    CTACTAATTG    AAGGGAAAA
       -130            ||||||        |||| ||||    ||||||||||     ||||||||      ||||||||
IFN-B  AATAAAGAG    TTTTAGAAAC    TACTAAAATG    TAATGACAT     AGGAAAACTG    AAGGGAGAA
                         -60           -50           -40           -30           -20
                                                        CAT                   CCATTCTTAA
E      AAG              GTTTGTGTGT    GAGGACCATC                AGTATAATA     |||||||||
                        ||||||||||    ||||||                    |||||||       AGGCCATACC
IFN-B  GTGAAAGTGG    GAAATTCCTC    TGAATAGAGA                TCATATAAAT
                         1            10            Hpa1          30
                                                   20
E      -10              AGAGACCTGT   GTTTGTGTGT    GTGTTAACAT    TTGAAAAAA
       CAAAAAGAAA       ||||          ||||||||     ||||||||       ||||||
IFN-B  CATGGAGAAA       GGACATTCTA   ACTGCAACCT    TTCGAAGCCT    TTGCTCTGGC
```

A: Peptide 284-303
B: Peptide 348-364 E16
N: Non-immune serum

Figure 16

SPECIFIC IMMUNOPRECIPITATION OF (2'-5') A SYNTHETASE
ACTIVITY BY ANTI-PEPTIDE ANTIBODIES

ENZYME ACTIVITY IMMUNOPRECIPITATED FROM

| DAUDI CELLS | | WISH CELLS | |
|---|---|---|---|
| ANTI-B cpm | ANTI-C cpm | ANTI-B cpm | ANTI-C cpm |
| 5,600 | 0 | 12,420 | 48,290 | mean of three experiments

Peptides: B C
E16, 40K
E18, 46K

Different forms of (2'-5') A synthetase in human cells and subfractions

Western blot
Anti OASE-B

Figure 22
DIAGNOSIS OF VIRAL INFECTION BY IMMUNOFLUORESCENCE STAINING
OF PERIPHERAL BLOOD MONONUCLEAR CELLS WITH ANTI-OASE SERUM
Healthy Donor          Viral Disease          Normal serum*
 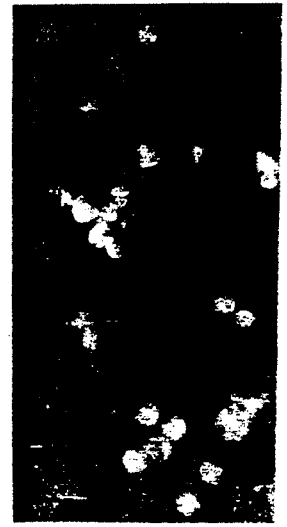 
Negative lymphocytes  Positive lymphocytes  *viral disease
                                            Negative lymphoc.

INTERFERON-INDUCED HUMAN (2'-5') OLIGO A SYNTHETASE

BACKGROUND OF THE INVENTION

This application is a continuation-in-part of U.S. Ser. No. 833,212, filed Feb. 25, 1986, which is a continuation-in-part of U.S. Ser. No. 601,782, filed Apr. 18, 1984, now abandoned the contents of both of which are hereby incorporated by reference.

Throughout this application, various publications are referenced by the name of the author and date of publication within parentheses. Full citations for these references may be found at the end of the specification listed in alphabetical order immediately preceding the claims. The disclosures of these publications in their entireties are hereby incorporated by reference into this application in order to more fully describe the state of the art as known to those skilled therein as of the date of the invention described and claimed herein.

Many of the biological effects of interferon (IFN) appear to be mediated by the induction of new mRNAs and proteins in cells exposed to IFNs (for review: Revel, 1984; Lebleu and Content, 1982; Baglioni and Nilsen, 1983). Among these IFN-induced proteins, two groups appear particularly important: 1) translation regulatory enzymes (ds RNA dependent protein kinase and (2'-5') oligo A synthetase, (2'-5') oligo A-activated nuclease, 2-phosphodiesterase); and 2) cell surface antigens (HLA-A, B, C, B2-microglobulin, HLA-DR). Other cellular and excreted proteins probably play important roles as well (Weil et al., 1983; Chebath et al., 1983; Wallach et al., 1983). With the exception of the HLA genes (Malissen et al., 1982; Schamboeck et al., 1983), the structure and sometimes the function of the IFN-induced proteins is unknown and so is the mechanism by which IFNs activate specifically these genes. To address these questions, several cDNAs from IFN-induced genes have been recently cloned (Chebath et al., 1983; Merlin et al., 1983; Friedman et al., 1984; Samanta et al., 1984). We have, in particular, studied the cDNA and gene coding for the human (2'-5') oligo A synthetase (OASE), a ds RNA-activated enzyme that converts ATP into ppp(A2'pA)n oligomers (Kerr and Brown, 1978) which in turn bind to and activate the latent RNAse F (Schmidt et al., 1978). The (2'-5') oligo A synthetase is strongly induced in cells by all three types of human IFNs, and its increase is a good marker of IFN activity (Wallach et al., 1982). The enzyme is induced during differentiation of hematopoietic cells, and denotes an autocrine secretion of IFN-beta (Yarden et al., 1984). The enzyme is similarly induced late in the S phase of synchronized embryo fibroblasts (Wells and Mallucci, 1985). The enzyme activity drops when cell growth starts (Etienne-Smekens et al., 1983; Creasey et al., 1983) and appears to be involved in the antigrowth effect of IFN (Kimchi et al., 1981). Deficiency in the (2'-5') oligo A synthetase or in the (2'-5') oligo A-activated RNAse F has also been correlated with partial loss of the antiviral effects of IFNs (Salzberg et al., 1983; Epstein et al., 1981), although this is probably not the only mechanism by which IFN inhibits virus growth (Lebleu and Content, 1982). The (2'-5') oligo A nucleotides have been detected in many eucaryotic cells and even in bacteria (Laurence et al., 1984) and the synthetase is likely to be a wide-spread enzyme. The enzyme has been purified from mouse (Dougherty et al., 1980) and human cells (Yand et al., 1981; Revel et al., 1981); a large and a small form of the enzyme have been observed (Revel et al., 1982; St. Laurent et al., 1983) but their structures were not elucidated.

The (2'-5') oligo A synthetase, induced in cells exposed to IFNs (Hovanessian et al., 1977; Zilberstein et al., 1978) has a number of unusual properties. Its main activity is the synthesis from ATP of 5'triphosphorylated short oligo A chains (of up to 15 A, with mainly dimers to pentamers), but in contrast to other RNA polymerases, it adds adenylate or one other nucleotide specifically to the 2'OH of adenylate in oligo A (Kerr and Brown, 1978; Samanta et al., 1980), or to other (oligo) nucleotides with a free 2'OH adenylate such as NAD Ball, 1980) or even tRNA (Ferbus et al., 1981). To be active, the enzyme has to bind to double-stranded RNA stretches of minimum 50 bp (Minks et al., 1979), and must therefore possess several binding sites: for nucleotide triphosphates, for 2'OH adenosine polynucleotides and for double stranded RNA. The enzyme binds to 2', 5' ADP-Sepharose (Johnston et al., 1980), to poly (rI)(rC)-Agarose (Hovanessian et al., 1977) and to Cibacron Blue-Sepharose (Revel et al., 1981). In different cells, the (2'-5') oligo A synthetase activity is in the cytosol (Revel et al., 1981) or in ribosomal salt washes (Dougherty et al., 1980), as well as in the nuclear sap (Nilsen et al., 1982b) and even in large amounts in the nuclear matrix. It is notable that cellular RNAs can replace poly (rI)(rC) for activation of the enzyme (Revel et al., 1980) and the synthetase may even have a role in Hn RNA processing (Nilsen et al., 1982a). Some (2'-5') oligo A synthetase is bound to plasma membranes and can be incorporated in budding virions (Wallach and Revel, 1980). These complex interactions may ensure a localized action of the (2'-5') oligo A system (Nilsen and Baglioni, 1983) and explain its multiple suggested roles in normal and virus-infected cells. The synthetase amounts to less than 0.1% of the proteins in IFN-treated cells, and its structure could not be determined directly.

SUMMARY OF THE INVENTION

The present invention concerns human DNA encoding an enzyme having (2'-5') oligo A synthetase activity. One form of the DNA has the nucleotide sequence set forth in FIG. 7A. Another form of the DNA has the sequence of nucleotides 1-1322 set forth in FIG. 7A which overlaps with the sequence of nucleotides 901-1590 set forth in FIG. 7B.

An enzyme having (2'-5') oligo A synthetase activity has the amino acid sequence set forth in FIG. 7A. Another enzyme having (2'-5') oligo A synthetase activity has the sequence of amino acids 1-364 set forth in FIG. 7A which overlaps with the sequence of amino acids 290-400 set forth in FIG. 7B.

A 1.6 kb and 1.8 kb RNA having nucleotide sequences complementary to the nucleotide sequences in FIGS. 7A and 7B have been isolated.

A method of monitoring the response of a patient to an interferon comprises measuring the concentration of (2'-5') oligo A synthetase mRNA in cells or body fluids of the patient by hybridizing to the mRNA DNA complementary thereto.

Antigenic peptides of the present invention have an amino acid sequence contained within the amino acid sequences set forth in FIGS. 7A and 7B. Antibodies raised against these antigenic peptides recognize and immunoprecipitate (2'-5') oligo A synthetase. Also provided are antibodies against all four of the 40 kd, 46 kd, 67 kd and 100 kd forms of (2'-5') oligo A synthetase, as well as antibodies against one of these forms which does not cross with the other three forms.

A method of monitoring interferon activity in a subject comprises measuring the amount of (2'-5') oligo A synthetase in a cell or body fluid of the subject at predetermined time intervals, determining the differences in the amount of said synthetase in the cell or body fluid of the subject within the different time intervals, and determining therefrom the amount of synthetase in the cell or body fluid of the subject and thereby the interferon activity of the subject. The synthetase may be measured by contacting the synthetase with an antibody of the present invention so as to form a complex therewith and determining the amount of complex so formed.

BRIEF DESCRIPTION OF THE FIGURES

FIG. 1 depicts the structure and sequence of (2'-5') oligo A synthetase $E_1$ cDNA clone 174-3:

FIG. 1B depicts the nucleotide sequence having the longest coding frame. The first T is nucleotide 92 following the tails of the insert (right end in A). The Sau 3A$_1$ site and the Eco Rl of the insert are at positions 129 and 480 respectively of the sequence shown.

FIG. 2 depicts the size and induction of $E_1$ specific mRNAs in SV80 and Namalva cells:

FIG. 2A depicts the hybridization of nick-translated [$^{32}$P]-cDNA of clone $E_1$ to electrophoretic blots of denaturated poly A$^+$-RNA from SV80 cells. The RNAs were prepared at the indicated hour after IFN-beta-1 addition. The apparent size of the RNA is indicated on the autoradiography. Left lane, rRNA markers.

FIG. 2B is the same as 2A with RNA from Namalva cells treated with IFN-alpha for the indicated time. Left lane: rRNA markers.

FIG. 5 depicts the time course of the induction of C56 mRNA by IFN:

FIG. 6 depicts the restriction map of cDNAs for the 1.6 and 1.8 kb (2'-5') oligo A synthetase mRNAs.

FIG. 6B depicts a map of the 1.8 kb cDNA. The lambda gt10 clone 48-1 was isolated using the PstI-PstI genomic fragment containing exon 8 of the 1.8 kb RNA (FIG. 9). Exons are numbered as for the 1.6 kb E cDNA. The truncated exon 7 is designated 7a.

FIGS. 7A and B depict the nucleotide sequence of the two (2'-5') oligo A synthetase cDNAs. The nucleotides of the 1.8 kb cDNA clone 48-1 are numbered as for the 1.6 kb cDNA clone 9-21. Amino acid numbering is given in parentheses. Translation starts at the first or second condon of the ATGATG sequence. Limits between exons are shown by vertical bars. (Glycos.) indicates a possible glycosylation site in E18. Single base variations, possibly allelic differences, were detected between clones or genomic DNA in the 1.6 kb sequence at 376 (T for C), 525 (G for A), 807 (G for C), 811 (A for G); in the 1.8 kb sequence at 1087 (G for A), 1115 (G for C).

FIG. 11 depicts the sequence of the human (2'-5') oligo A synthetase promoter region. The sequence of the Sau3A-Hpal segment of FIG. 10 shown, aligned for comparison with the promoter region of the human IFN-beta-1 gene (Degrave et al., 1981). Numbering is from the presumed cap site. A purine-rich transcription-regulatory sequence around −75 in the IFN-beta-1 promoter (Zinn et al., 1983), repeated at −10, is underlined. The TATA box is doubly underlined.

FIG. 16 depicts the (2'-5') oligo A synthetase activity which is adsorbed on anti-B and anti-C IgG-Protein A-Sepharose was measured as described in Example 13. The scheme underneath shows the position of peptide B and peptide C in the two (2'-5') oligo A synthetase forms E16 and E18 sequenced by Benech et al. (1985b). The blackened area indicates the part of E18 which differs from the E16 molecule.

FIG. 22 depicts the use of the anti-B for immunofluorescence microscopic detection of elevated (2'-5') oligo A synthetase levels in lymphocytes from blood of patient with viral disease (middle panel). Right: control with normal serum; left: blood from healthy donor with anti-B strain. (lymphocytes do not stain, only macrophages or granulocytes give unspecific background).

DETAILED DESCRIPTION OF THE INVENTION

Figure 1A:
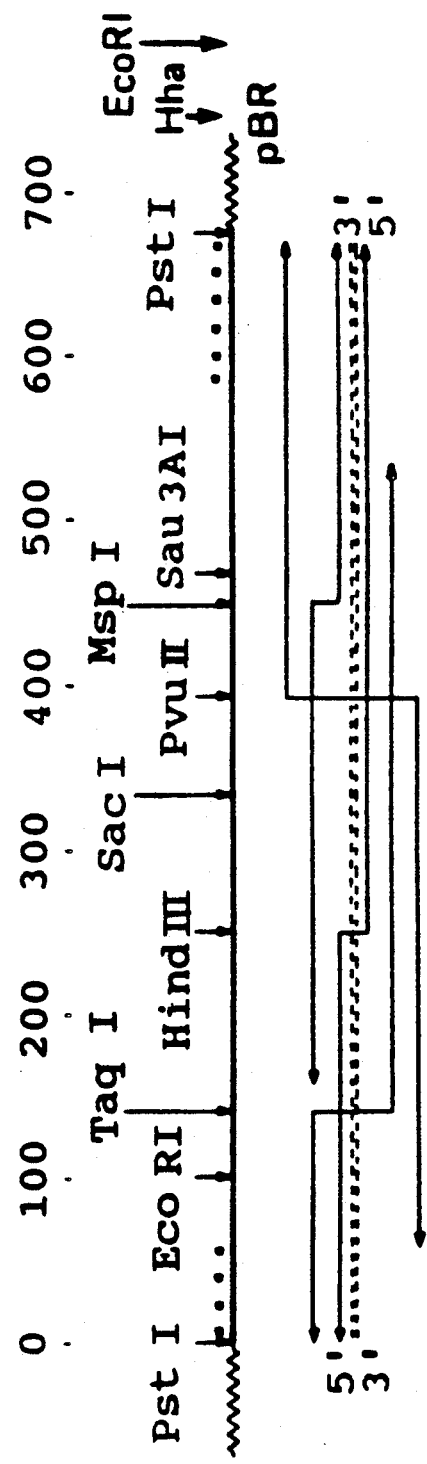
FIG. 1A depicts the restriction map of $E_1$ cDNA clone 174-3. The insert base pairs are numbered in the same direction as pBR322 DNA. The pBR Eco Rl site is on the right. Both strands of the insert (dotted lines) were sequenced (Maxam & Gilbert, 1980) from the restriction sites indicated by the vertical lines. The coding strand is 5' to 3' from right to left. Following the right PstI site there were 17G and 72T, followed by the dinucleotide GA and the 3T of the sequence shown in (B) which are therefore not part of the tails. At the 3' end, tails of 45A and 10C preceded the left PstI site.

The present invention concerns human DNA encoding an enzyme having (2'-5') oligo A synthetase activity and having the nucleotide sequence set forth in FIG. 7A. The DNA may also comprise the sequence of nucleotides 1-1322 set forth in FIG. 7A and the overlapping sequence of nucleotides 901-1590 set forth in FIG. 7B. The DNA of the present invention has the restriction enzyme sites set forth in FIG. 9.

An enzyme having (2'-5') oligo A synthetase activity has the amino acid sequence set forth in FIG. 7A. This enzyme comprises about 364 amino acids and has a molecular weight of about 41,500 daltons. Another enzyme having (2'-5') oligo A synthetase activity comprises the sequence of amino acids 1-364 set forth in FIG. 7A and the sequence of amino acids 290-400 set forth in FIG. 7B. This enzyme comprises about 400 amino acids and has a molecular weight of about 46,000 daltons.

The present invention provides a 1.6 kb RNA having a nucleotide sequence complementary to the nucleotide sequence set forth in FIG. 7A. Also provided is a 1.8 kb RNA comprising a nucleotide sequence complementary to the sequence of nucleotides 1-1322 set forth in FIG. 7A and the sequence of nucleotides 901-1590 set forth in FIG. 7B.

A transfer vector of the present invention comprises lambda-gt 11-E16 DNA of the present invention, and the lac Z gene, the DNA being fused in phase with the lac Z gene so as to enable expression of the DNA in the suitable host cell. A microorganism may be transformed by the transfer vector. Escherichia coli is a suitable microorganism for the transformation.

A method of monitoring the response of a patient to an interferon comprises measuring the concentration of (2'-5') oligo A synthetase mRNA in cells or body fluids of the patient by hybridizing to the mRNA DNA complementary thereto. The mRNA may be the 1.6 kb or 1.8 kb RNA of the present invention.

A method for evaluating the response of cells and tissues to interferon comprises hybridizing RNA from cells or tissues exposed to interferon with cDNA complementary to the RNA, and determining the extent of hybridization. The RNA is extracted from cells or tissues which have been exposed to interferon, immobilized on a membrane filter and hybridized to labeled cDNA specific for interferon-induced mRNAs. The method may also comprise in situ hybridization of labeled cDNA to slices of tissues and then evaluating by microscopic examination autoradiography, or fluorescence. The cells or tissues analyzed may be of human or other animal origin.

A kit for carrying out a method for evaluating the response of cells and tissues to interferon contains a cDNA complementary to a sequence set forth in FIG. 7A or 7B, reagents to carry out the hybridization tests for nick-translation with deoxy ribonuclease I and [$^{32}$P]-gamma -dCTP, reaches for hybridization on nitrocellulose membranes, and reagents for RNA extraction from cells.

Also provided are antigenic peptides having amino acid sequences contained within the amino acid sequences set forth in FIG. 7A and FIG. 7B.

An antigenic peptide of the present invention has the amino acid sequence comprising the 17 C-terminal amino acids of the amino acid sequence set forth in FIG. 7A and having the amino acid sequence: ARG-PRO-PRO-ALA-SER-SER-LEU-PRO-PHE-ILE-PRO-ALA-PRO-LEU-HIS-GLU-ALS. Another antigenic peptide has the amino acid sequence: GLU-LYS-TYR-LEU-ARG-ARG-GLN-LEU-THR-LYS-PRO-ARG-PRO-VAL-ILE-LEU-ASP-PRO-ALA-ASP.

Antibodies raised against the antigenic peptides of the present invention recognize and immunoprecipitate (2'-5') oligo A synthetase. In one embodiment of the invention, the antibody is specific for all four of the 40 kg, 46 kd, 67 kd and 100 kd forms of (2'-5') oligo A synthetase. In one embodiment of the invention, the antibodies are obtained by immunizing an animal with the antigenic peptide GLU-LYS-TYR-LEU-ARG-ARG-GLN-LEU-THR-LYS-PRO-ARG-PRO-VAL-ILE-LEU-ASP-PRO-ALA-ASP. In another embodiment of the invention, the antibody is conjugated with a label, e.g., a fluorescent label, a radioactive label or an enzyme.

This antibody may be used in an assay, e.g., a fluorescent immunoassay, a radioimmunoassay or an enzyme immunoassay, for the 40, 46, 67 and 100 kd forms of (2'-5') oligo A synthetase in cells. This assay comprises incubating the cells with the labeled antibody and detecting cells being (2'-5') oligo A synthetase in any of the 40, 46, 67 and 100 kd forms by detecting the label. In one embodiment of the invention, the cells are mononuclear blood cells.

The present invention also provides a kit for the detection of all four forms of (2'-5') oligo A synthetase which comprises the antibody of the present invention against the 40, 46, 67 and 100 kd forms of (2'-5') oligo A synthetase.

The invention further provides a 67 kd (2'-5') oligo A synthetase protein in a state of enhanced purity. Moreover, a 100 kd (2'-5') oligo A synthetase protein in a state of enhanced purity is also provided.

The present invention additionally provides an antibody against one of the 40 kd, 46 kd, 67 kd or 100 kd forms of (2'-5') oligo A synthetase which does not crossreact with the other three forms.

A method of monitoring interferon activity in a subject comprises measuring the amount of (2'-5') oligo A synthetase in a cell or body fluid of the subject at predetermined time intervals, determining the differences in the amount of said synthetase in the cell or body fluid of the subject within the different time intervals, and determining therefrom the amount of synthetase in the cell or body fluid of the subject and thereby the interferon activity of the subject. The amount of synthetase may be measured by contacting the synthetase with an antibody of the present invention so as to form a complex therewith and determining the amount of complex so formed.

A method of monitoring interferon activity may further comprise, extracting (2'-5') oligo A synthetase from a cell or body fluid which has been exposed to interferon, labeling the extracted synthetase with an identifiable marker to form a labeled synthetase, contacting the labeled synthetase with an antibody of the present invention under suitable conditions so as to form a labeled-synthetase-antibody complex, and detecting the marker in the complex, thereby detecting the synthetase. The marker may be $^{35}$S-methionine.

A kit for carrying out the method of monitoring interferon activity comprises an antibody of the present invention, materials for extracting the synthetase, materials for labeling the synthetase, and materials for detecting the marker and determining the amount of synthetase.

The present invention also provides cloned DNA that specifically hybridizes to messenger RNAs which appear in human cells after exposure to interferon. The cloned cDNA may be specific for the (2'-5') oligo A synthetase mRNAs of 3.6, 1.8 and 1.6 kilobase. A cloned DNA of the present invention is specific for the mRNA of a 56,000 Mr-protein, which mRNA is 2 kilobase and which has the sequence defined in FIG. 1.

A partial cDNA clone (E1) for the (2'-5') oligo A synthetase mRNA from human SV80 cells, was first obtained through its ability to select by hybridization an mRNA producing 2'-5') oligo A synthetase activity upon translation in *Xenopus laevis* oocytes (Merlin et al., 1983). The E1 cDNA insert (675 bp) hybridizes to 3 RNA species of 1.6, 1.8 and 3.6 kb which are coinduced by IFN in SV80 cells, accumulate for 12 hours and are found in the cytoplasmic polysomal fraction (Benech et al, 1985). Two other early transcripts (2.7 and 4 kb) appear in lesser amounts. Analysis of various types of human cells has shown that these RNAs are differentially expressed in a cell specific manner. In B lymphoblastoid cells (Namalva, Daudi) only the 1.8 kb RNA accumulates, while in amniotic WISH cells, in histiocytic lymphoma U937 cells and in HeLa cells, the 1.6 kb RNA is predominantly induced by IFN with some 3.6 kb RNA, but little 1.8 kb RNA. In diploid fibroplasts FSll, in SV80 fibroplastoid cells and in the T cell line CEMT, all 3 stable RNAs are expressed (Benech et al., 1985). The type of (2'-5') oligo A synthetase RNA expressed does not depend on the species of IFN used (alpha, beta, or gamma) but rather seems developmentally regulated in the cell.

The different (2'-5') oligo A synthetase transcripts appear to originate from a single gene (Benech et al., 1985). Restriction mapping showed: 1) that the E1 cDNA corresponds to the 3' end of the 1.6 kb RNA; 2) that the 1.8 kb RNA has a different 3' end than the 1.6 kb RNA and contains an additional downstream exon; and 3) that the 3.6 kb RNA has the same 3' end as the 1.8 kb RNA but is incompletely spliced. Hybridization-translation experiments using specific genomic DNA fragments also demonstrate that both the 1.8 and 1.6 kb RNAs actively code for (2'-5') oligo A synthetase (Benech et al., 1985).

cDNA clones for the 1.6 and 1.8 kb RNAs have been isolated and sequenced, which enabled the deduction of the amino acid sequences of two forms of the IFN-induced (2'-5') oligo A synthetase in human cells. The two proteins differ in their C-termini, which is hydrophobic in the 1.6 kb RNA product (E16) and acidic in the 1.8 kb RNA product (E18). A complete mapping of the (2'-5') oligo A synthetase gene shows that the 1.6 kb RNA is coded by 7 exons and the 1.8 kb RNA by 8 exons. The sequence of the presumed transcription initiation site and promoter region of the IFN-activated human (2'-5') oligo A synthetase gene shows a striking homology to the promoter region of the human IFN-beta-1 gene.

Two peptide sequences were chosen from the total amino acid sequences of E16 and E18 to serve as antigens for the induction of antibodies against the active (2'-5') oligo A synthetase molecule. Peptide B, having the sequence:

GLU-LYS-TYR-LEU-ART-ARG-GLN-LEU-
THR-LYS-PRO-ARG-PRO-VAL-ILE-LEU-
ASP-PRO-ALA-ASP comprises amino acids 284 to 303 common to both the E18 and the E16 sequences (Benech et al., 1985b). Peptide C, having the sequence:

ARG-PRO-PRO-ALA-SER-SER-LEU-PRO-
PHE-ILE-PRO-ALA-PRO-LEU-HIS-GLU-
ALA comprises the C terminus of E16, i.e., residues 348 to 364.

Both peptides were synthesized by the solid-phase peptide synthesis method of Barany and Merrifield (1980). After purification on Sephadex G25 columns in 2 M acetic acid, the peptides were linked to Keyhole Limpet Hemocyanin (Calbiochem). Fsterification of the $NH^2$-terminal arginine of peptide C with p-aminophenylacetic acid allowed to covalently link the peptide to the carrier protein through its amino-terminus (Spirer, et al., 1977). Peptide B was coupled to the carrier protein by ethylene diamine carbodiimide (Hoare and Koshland, 1967).

Rabbits were injected subcutaneously with 1 mg carrier-coupled peptide (equivalent to 0.2 mg pure peptide) which was emulsified in complete Freund's adjuvant. Rabbits were boosted twice at two week intervals with 0.5 mg of carrier-coupled peptide in incomplete adjuvant. Subsequent boosting was done by injection of 0.1 mg carrier-free peptide in incomplete adjuvant, and was continued until maximal antibody response. The titer of antibodies in the rabbit sera were measured in enzyme-linked immunosorbent assays (Green, et al., 1982) using the carrier-free peptides.

The fibroblastoid cell line SV80 and the amniotic cell line Wish were grown to confluent monolayers on plastic dishes and the Daudi cell line was grown in suspension to $1.5 \times 10^6$ cells/ml (Benech, et al., 1985a). Cultures were treated for 16-24 hours with rIFN-$\beta$1, 500 U/ml. The human rIFN-$\beta$1 was produced by genetically engineered CHO cells and purified to homogeneity by monoclonal antibody affinity chromatography (Chernajovsky, et al, 1984).

Cells were washed twice with phosphate buffered saline (PBS) at 4° C. and lysed in the cold in Buffer A (20 mM Hepes buffer, pH 7.5, 5mM magnesium acetate, 30 mM$\beta$-mercaptoethanol, 100 $\mu$M phenylmethyl sulfonyl fluoride (PMSF), 10% glycerol and 0.5% Nonidet P-40 (NP40)). Nuclei and unbroken cells were eliminated by centrifugation at 1,500 $\gamma$ for 10 minutes. The supernatant (Sl.5) was centrifuged 10 minutes at 15,000 $\gamma$ in an Eppendorf Microfuge to obtain a mitochondria and lysosome-free supernatant (Sl.5). Protein concentrations were measured by microassays (Bradford, 1976).

Centrfigutation of S15 for 2 hours at 100,000 $\gamma$ in a Beckman refrigerated ultracentrifuge was used to prepare cell sap (S100) and microsome (P100) fractions Alilquots of S15 containing 1-2 $\mu$g protein were incubated in 20 $\mu$l reactions containing 25 mM Hepes buffer, pH 7.5, 20 mM magnesium acetate, 1 mM dithiothreitol, 1.5mM ATP, 4 $\mu$Ci of $^{32}$P-$\alpha$-ATP, 50 $\mu$g/ml poly(-rI)(rC) (from PL-Biochemicals) for 2 hours at 30° C. After boiling for 5 minutes and microfuge centrifugation, bacterical alkaline phosphatase was added at 25 U/ml to an aliquot and the reaction incubated for 2 hours at 37° C. From 2 to 7 $\mu$l were spotted on Whatman 3 MM paper and analyzed by electrophoresis at 3,000 V in pyridine/acetic acid, pH 3.5. After autoradiography, the (A2'p)nA oligomer spots were cut out and counted.

Aliquots of crude cellular factions (30 $\mu$g protein) were adjusted with Laemmli's sodium-dodecyl-sulphate-polyacrylamide gel electrophoresis loading buffer (Laemmli, 1970) and boiled 10 minutes before electrophoresis on 7.5 or 10% gels. Amersham's $^{14}$C-methylated proteins were used as molecular weight standards ($10^4$ cpm) Electrophoretic transfer onto nitrocellulose paper (Schleicher and Schuell BA85) was carried out in 25 mM Tris-base, 192 mM glycine and 20% methanol. The blots were preincubated in 0.9M NaCl, 0.01M Tris-HCl, pH 7.5, 10% (v/v) of a 1% fat milk solution, 10% (v/v) heat-inactivated fetal calf serum and 0.05% Tween-20, either for 2 hours at 37° C. or overnight at 4° C. followed by 30 minutes at 37° C. Blots were then incubated with anti-(2'-5') oligo A synthetase peptide B antibodies in form of rabbit IgG 0.01 mg/ml, for 2 hours at 37° C. Blots were washed 5 times for 10 minutes in 4% fetal calf serum and incubated in the complete above preincubation mixture containing $10^6$ cpm/ml of 125I-protein A (Amersham, 30 mCi/mg}for 1 hour at 37° C. Blots were washed and subjected to autoradiography.

First aliquots of 5-10 $\mu$l anti-(2'-5') oligo A synthetase peptide B rabbit serum were adsorbed on 3mg of Protein A-Sepharose (Pharmacia) equilibrated in PBS with 3% bovine serum albumin (BSA), for 30 minutes at room temperature, then washed with PBS-1% BSA. For immunoprecipitation of the (2'-5') oligo A synthetase enzymatic activity, aliquots of 2$\mu$g of S15 proteins in a final volume of 20$\mu$l of buffer A were adsorbed on the above pelleted IgG-Protein A Sepharose for 2 hours at 4° C. The suspension was diluted 5 fold in Buffer A and the supernatant transferred to another tube. The pellet was washed 3 times with 0.5 ml Buffer A and was then suspended in 25 $\mu$l of the enzyme reaction mixture (see above). Activity was measured also on aliquots of the non-bound supernatant.

For labeling (2'-5') oligo A synthetase, Wish cells were grown to confluent monolayers on 3 cm plastic dishes and treated for 12 hours with 500 U/ml rIFN-$\beta$1. The medium was replaced by 0.5 ml methionine-free DMEM (GIBCO) containing 500 $\mu$Ci of $^{35}$S-methionine (Amersham 400 mCi/mmol) and cells incubated for 2 hours, washed with PBS and homogenized in Buffer A. The S15 was used for immunoprecipitation. About $10^7$ cpm of S15 proteins were added to the pelleted Protein A-Sepharose and mixed for 2 hours at 4° C. The beads were washed with 1% BSA, 1% NP40, 2M KCl in PBS and twice with PBS only. Samples were analyzed by sodium-dodecyl-sulphate-polyacrylamide gel electrophoresis.

EXAMPLE 1

Measure of (2'-5') oligo A synthetase mRNA by cDNA clones

A) Isolation of E-cDNA clones

Total RNA was prepared from SV80 cells (SV40-transformed human fibroblasts) treated for 12 hours with 200 units per ml IFN-beta. The RNA was extracted by 3M LiCl - 6M urea and purified by passage on oligo dT-cellulose. The 0.4 mg poly A+-RNA obtained were fractionated in a preparation of gel electrophoresis apparatus in 1.5% agarose/6M urea 25 mM sodium citrate pH 3.5. The 17-18S RNA fraction, was used to prepare cDNA as follows: 2 micrograms RNA were heated for 1 min at 90° C. with 2 micrograms oligo $(dT)_{12-18}$ in 60 microliters water, cooled at 0° C., supplemented with salts to a final concentration of 50 mM Tris-HCl pH 8.3, 10 mM $MgCl_2$, 75 mM KCl and incubated 5 min at 42° C. before adding 1 mM dithiothreitol, 1 mM each dATP, dIGP, 0.5 mM dCTP, 20 micro-Ci $^{32}$P-dCTP (300 (Ci/mmol)), 4 mM Napyrophosphate and 20 units reverse transcriptase in a final volume of 0.1 ml. The mixture was incubated for 45 minutes at 42° C., the reaction was stopped with 10 mM EDTA, 0.2% Na-dodecyl sulfate and the cDNA extracted with phenol-chloroform, treated with 0.3N NaOH for 2 hours at 52° C. and neutralized. The cDNA was filtered on Sephadex G-75, ethanol precipitated, and tailed by dATP with terminal transferase. The synthesis of the second cDNA strand was primed with oligo (dT) and carried out as for the first strand for 2 hours at 42° C. but without radioactive nucleotide and without pyrophosphate. To insure blunt ends the ds cDNA was incubated with E. coli DNA polymerase I large fragment first in 20 mM Tris-HCl pH 8, 75 mM KCl, 5 mM MgCl, 1 mM dithiothreitol for 5 minutes at 37° C. (trimming reaction) and then under the conditions of filling-in with ATP. The ds cDNA was fractionated by sedimentation on a 5-20% sucrose gradient and the heaviest fractions were tailed with dCTP and annealed with equimolar amounts of PstI-cut pBR322 plasmid DNA tailed with dCTP. About 7 ng DNA were mixed with 100 microliters of frozen, CaCl2-treated, E. coli MM294. After 30 minutes at 0° C., and 5 minutes at 37° C., the bacteria were grown in 2ml of LB-broth for 2 hours at 37° C., and plated on LB-agar plates with 10 micrograms/ml tetracycline. About $1.4 \times 10^5$ tetracycline-resistant, ampicillin-sensitive colonies were obtained per microgram recombinant plasmid DNA.

To identify the cDNA clone of the (2'-5') oligo A synthetase mRNA, a total of 3,000 plasmid DNA clones were screened by hybridization to RNA of IFN-treated SV80 cells, and the DNA-selected RNA was tested by injection into Xenopus laevis oocytes and a measure of the (2'-5') oligo A synthetase activity formed according to the method of Shulman and Revel (1980). Pools of plasmid DNA from 12 individual clones (3 micrograms DNA each; cut with Eco Rl) were applied onto a 0.4 cm diameter nitrocellulose filter and prehybridized for 2 hours at 37° C. in 50% formamide, 2 mM Pipes buffer pH 6.4, 0.75M NaCl, 1 mM EDTA (buffer A). Three filters with pBR322 DNA and thirty filters of recombinant DNA pools were incubated together with 300 micrograms poly A+-RNA [calculated to have a 10-fold excess of each insert cDNA over the presumed amount of (2'-5') oligo A synthetase mRNA, 0.09 micrograms or 0.03%] in 1 ml buffer A for 20 hours at 37° C. The filters were washed twice at 37° C. with buffer A, 4 times in 20 mM Tris-HCl pH 7.5, 0.15M NaCl, 1 mM EDTA, 0.5% Na dodecyl sulfate (once at 37° C. and 3 times at 52° C.) and then 4 times with 10 mM Tris-HCl pH 7.5, 1 mM EDTA (buffer C) at 52° C. Each filter was next washed individually in buffer C at 52° C. and the RNA was eluted by heating 2 min at 96° C. in 0.3 ml buffer C with 40 micrograms rabbit liver tRNA per ml. After quick cooling the ethanol precipitation, the RNA was dissolved in 2 microliters water. Ten Xenopus laevis oocytes were microinjected with 0.7 microliters RNA and after 18 hours at 19° C., the oocytes were homogenized in their incubation medium (Shulman and Revel, 1980) and 0.15 ml of homogenate was mixed with poly (rI) (rC)-agarose beads. The beads were incubated for 16 hours at 30° C. with 2.5 mM [$^{32}$P]-alpha-ATP (0.3 Ci/mmol), 10 mM dithiothreitol, and 10 microliters of the liquid phase were incubated with 0.35 units bacterial alkaline phosphatase in 30 mM Tris-base for 60 minutes at 37° C. The idgest was submitted to paper electrophoresis on Whatman 3 MM paper at 3,000 V for 4 hours, and the spots corresponding to (2'-5') ApA and (2'-5') ApApA were cut and counted by scintillation. From the DNA-selected RNA, 1 microliter was used for in vitro translation in a reticulocyte lysate as described in Weissenbach et al. (1979), to measure the total mRNA activity of the sample.

The ratio of (2'-5') oligo A synthetase activity over total mRNA activity in the DNA-selected RNA samples was calculated for each filter. One filter with pool 174, out of the 250 pools of 12 individual plasmids, gave consistently a ratio about 10 times higher as other pools or as pBR322 DNA. The plasmid DNA of each individual clone of pool 174 was tested on separate filters and clone 174-3 was found to give consistently a 35-100 fold enrichment of the (2'-5') oligo A synthetase mRNA over total mRNA as compared to total RNA or pBR322 DNA-selected RNA (Table 1). Clone 174-3 was identified as the (2'-5') oligo A synthetase cDNA and designated E-cDNA. The structure and sequence of this cDNA is shown in FIG. 1. The E-cDNA clone contains the sequence for the 100 carboxy terminal amino acids of the enzyme and a 192 nucleotide-long untranslated region preceding the poly A-tail.

TABLE 1

IDENTIFICATION BY HYBRIDIZATION-TRANSLATION OF THE CLONE OF (2'-5') OLIGO A SYNTHETASE cDNA
E mRNA activity measured by oocyte injection (2) of induced RNA

|  | Expt. 1 | | Expt. 2 | | Expt. 3 | |
| --- | --- | --- | --- | --- | --- | --- |
|  | (2'-5') oligo A cpm | (specific activity)* | (2'-5') oligo A cpm | (specific activity)* | (2'-5') oligo A cpm | (specific activity)* |
| Total poly. A+-RNA | 4050 | (0.007) | 3440 | (0.004) | 4900 | (0.01) |
| RNA selected on: | 350 | . | 570 | (0.03) | 670 | (0.02) |
| pBR filters | 625 | (0.05) | 595 | | 725 | |

TABLE 1-continued
IDENTIFICATION BY HYBRIDIZATION-TRANSLATION OF THE CLONE OF (2'-5') OLIGO A SYNTHETASE cDNA
E mRNA activity measured by oocyte injection (2) of induced RNA

|  |  | Expt. 1 | | Expt. 2 | | Expt. 3 | |
| --- | --- | --- | --- | --- | --- | --- | --- |
|  |  | (2'-5') oligo A cpm | (specific activity)* | (2'-5') oligo A cpm | (specific activity)* | (2'-5') oligo A cpm | (specific activity)* |
| plasmid pool 174 | | 2320 | | — | | — | |
| other pools | | 230** | ±60 | — | | — | |
| Clones of pool 174: | 1 | 560 | | 700 | | 995 | |
| | 2 | 625 | | 950 | (0.34) | 825 | |
| | 3 | 6460 | (4.78) | 39,800 | (2.7) | 11,235 | (0.75) |
| | 4 | 600 | | 1,820 | (0.48) | 1,030 | (0.03) |
| | 5 | 745 | | 500 | (0.49) | 530 | |
| | 6 | 985 | | 475 | | 630 | |
| | 7 | 1270 | (0.1) | 365 | | 605 | |
| | 8 | 395 | | 800 | (0.02) | 600 | |
| | 9 | 490 | | 100 | | 1,030 | (0.03) |
| | 10 | 1465 | (0.14) | 290 | | 1,155 | (0.06) |
| | 11 | 1860 | (0.27) | 365 | | 735 | |
| | 12 | 540 | | 320 | | 915 | |
| No RNA | | 195 | | 185 | | 590 | |

*Specific activity ratio of (2'-5') oligo A synthesis or mRNA-infected oocytes to translation of same RNA in reticulocyte lysates.
**Average of 28 pools.

B) Measure of interferon-induced (2'-5') oligo A synthetase mRNA by hybridization of E-cDNA Plasmid DNA of clone 174-3 (E-cDNA) can be used to detect the complementary RNA on electrophoretec blots of total cell RNA. Poly $A^{30}$-RNA is prepared from SV80 cells treated various times by 2000/ml interferon-beta and 7 micrograms RNA are denatured in 50% formamide, 6% formaldehyde, electrophoresed in 1.3% a9arose with 6% formaldehyde and blotted onto nitrocellulose according to the procedures of Thomas (1980) and Fellous et al. (1982). The E-cDNA plasmid labeled by nick-translation with according to Merlin et al. (1983), is hybridized to the nitrocellulose blot.

In SV80 cells, three RNA species which are all coordinately induced by the interferon treatment, hybridize with E-cDNA (FIG. 2), a large RNA species of 3.6 kilobases and 2 smaller species of 1.85 and 1.65 kilobase. In non-treated SV80 cells, no E-specific RNA is found. The 3 RNA species appear at 4 hours, are maximum at 12 hours and decrease slowly thereafter. The RNAs are still clearly detected at 24 hours after interferon. Additional RNA species seen only at 4 hours are most probably precursors of the more stable species. The same 3 RNA species are seen in human diploid fibroblasts treated by interferon. However, in cells of the hemopoietic lineage such as lymphoblastoid Namalva cells, only one main RNA species hybridizes to E-cDNA (FIG. 2) and corresponds to the 1.85 kilobase RNA species. The same RNA pattern is seen in other lymphoblastoid cells, in erythroid HL-60 and in promonocyte U937 cells.

The different E-specific RNA pattern in fibroblasts and lymphoid cells corresponds to different forms of the (2'-5') oligo A synthetase in these cells. Lymphoid cells contain an enzyme of molecular weight 30,000 daltons, while fibroblasts contain two forms of the enzyme of molecular weight 80,000 and 30,000 daltons, as reported by Revel et al. (1982). The small 1.85 kilobase mRNA is sufficiently long to code for the 30,000 Mr enzyme but not for the larger form, while the 3.6 kilobase E-mRNA codes for the 80,000 Mr form of the enzyme. All three E-specific RNA species hybridize to a single clone of human genomic DNA, and probably originate from a single gene, the 3.6 kilobase RNA having an additional interferon exon as compared to the 1.85 kilobase RNA.

Leucocyte interferon-alpha induces E-specific RNA as well as does fibroblast interferon-beta. The multiplicity of RNA species revealed by hybridization to EcDNA suggests that different interferon species, which all induce (2'-5') oligo A synthetase, could induce different forms of the RNA and of the enzyme. Different interferon species can also vary in their efficacy for inducing E-mRNA.

RNA to be treated in the above hybridization assay to E-cDNA may be prepared from various cells in culture or from tissues taken from patients receiving interferon therapy or suffering from viral diseases or from disease in which an elevated (2'-5') oligo A synthetase was observed (Schattner et al., 1981). RNA may also be prepared from blood cells, such as leukocytes, obtained from peripheral blood. The electrophoretic blot can be replaced by a dot-hybridization method, in which RNA samples are directly applied to nitrocellulose in circles or rectangles of defined area, and the radioactive cDNA is hybridized to the nitrocellulose sheet. The radioactivity of each circle of rectange is then measured by direct counting or by autoradiography followed by screening of the autoradiographic film.

An alternative method is to perform hybridization in situ on tissue slices obtained from biopsies of tissues exposed to interferon. This can be preferentially applied to brain biopsies in patients receiving interferon for a brain viral disease or tumor, in order to measure whether the brain has been exposed to interferon when the drug is given either by intrathecal injection or by systemic injection. The method may be applied to skin biopsies when the interferon treatment is given locally as an ointment for skin lesions. It is obvious that many other application are possible. The tissue slices may be fixed and hybridized in situ to radioactive DNA, followed by an autoradiography with a sensitive photographic emulsion. The cDNA may also be labeled by fluorescent nucleotides or by modified nucleotides which can bind fluorescent molecules, and the hybridization to the tissue slice can be monitored by fluorescent microscopy.

An increase in hybridization of the E-cDNA was compared to a proper control cell RNA or tissue sample, indicating that the cell or tissue has been exposed to interferon. The rapidity (4-24 hours) and sensitivity (1-200 units of interferon per ml) of the method makes it very useful to follow a treatment by external interferon, or formation of endogenous interferon in blood and tissue of patients.

EXAMPLE 2

Cloned cDNA for the interferon-induced 56,000 Mr protein

A) Isolation of cloned C56-cDNA

Figure 3:
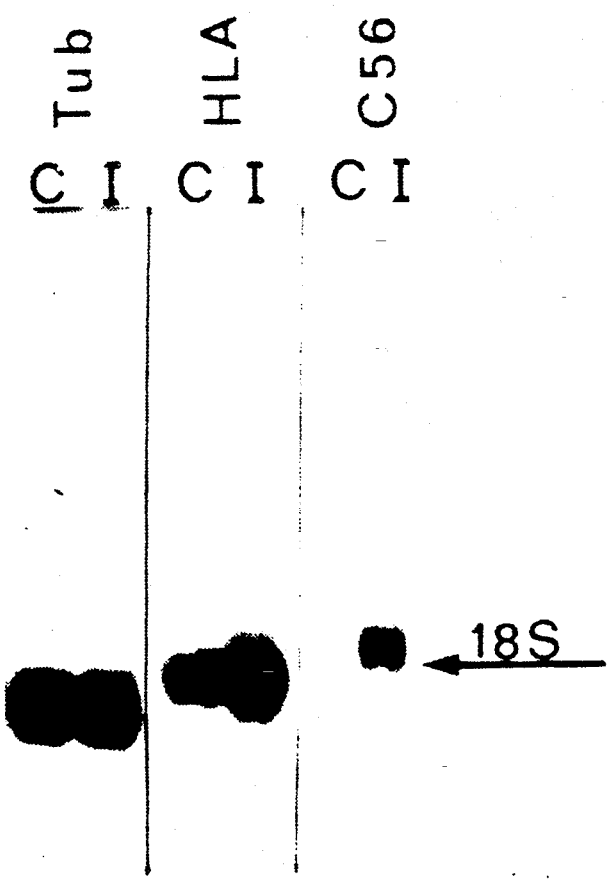
FIG. 3 depicts the characterization by hybridization to RNA blots of recombinant plasmid clone C56, harbouring cDNA for an IFN-induced mRNA Poly (A)+ RNA from IFN-treated SV80 cells (I) or from non-treated cells (C), 7 micrograms were electrophoresed on agarose gels and after blotting to nitrocellulose were hybridized to nick-translated [$^{32}$P]-plasmid DNA of either the C56 clone, a human HLA cDNA clone or a rat tubulin cDNA clone. Exposure was for 48 h. Position of radioactive 18S ribosomal RNA marker is indicated.

The cloned cDNA was isolated from the library of recombinant plasmids described in Example 1. The principle of the method used was differential hybridization. Two duplicate sets of the 3,000 bacterial clones grown on nitrocellulose filters were hybridized either to [$^{32}$P]-cDNA from 17S-18S poly A+-RNA of SV80 cells treated by interferon-beta(200 U per ml), or to [$^{32}$P]-cDNA from total poly A+-RNA of non-treated SV80 cells. The radioactive cDNA were reverse transcribed from mRNA as in Example 1. About 40% of the bacterial clones hybridized strongly to the "interferon-treated" cDNA probe and 8% 9ave a clear differential signal, hybridizing preferentially or uniquely to the "interferon-treated" cDNA as compared to the "non-treated" cDNA. The latter group of clones was then screened by hybridizing the plasmid DNA from each clone, labeled radioactively by nick-translation, to electrophoretic blots of RNA from interferon-treated SV80 cells and from non-treated cells. By this criterion, 1-2% of the original 3,000 bacterial clones were found to contain a plasmid cDNA clone corresponding to an interferon-induced mRNA. One of these plasmid cDNA clones, designated C56, showed a particularly strong differential hybridization. This C56 DNA hybridizes to an 18S RNA present in interferon-treated cells but completely absent from control cell RNA (FIG. 3). In comparison, HLA-A,B,C mRNA which is increased 5-fold in SV80 cells after interferon-treatment (Fellous et al., 1982), appears much less induced than C56 mRNA and under the experimental conditions of FIG. 3, gives a clear signal also with "non-treated" RNA.

Figure 4A:
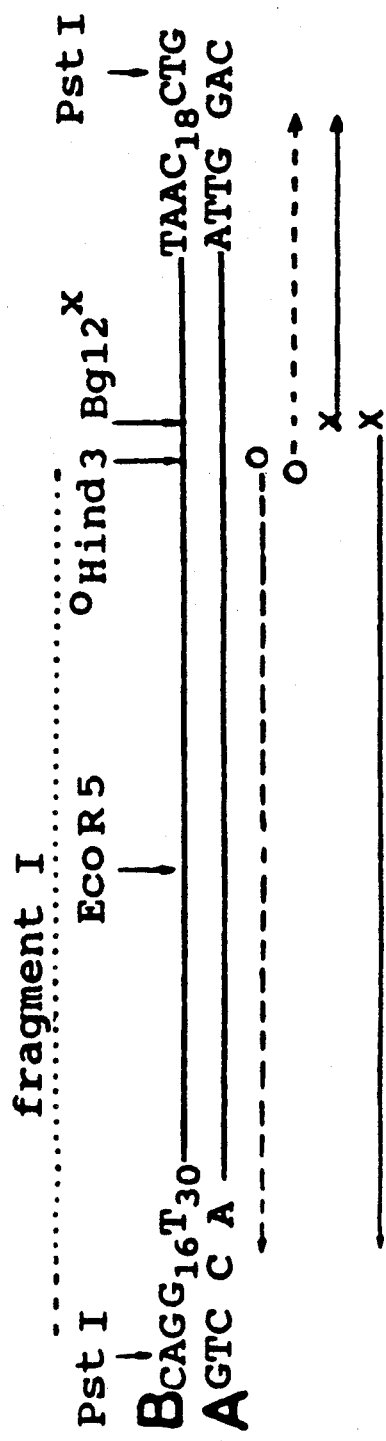
FIG. 4 depicts the partial restriction map and nucleotide sequence of the C56 450 bp insert. The C56 plasmid was digested with Hinc 3, end-labeled with alpha-[$^{32}$P]-dCTP by the DNA polymerase I-large fragment (Klenow enzyme, Boehringer) and the Hind 3-Pst 1 fragments were separated on a 1% agarose gel. In order to sequence the complementary strand, the plasmis was 5'-labeled at the Bgl 2 site with gamma [$^{32}$P]-ATP by the T$_4$-polynucleotide kinase (Biolabs) and the Bgl 2-PstI fragments were isolated. Sequencing was made by the Maxam and Gilbert technique. Sequence of coding strand A (right to left) is shown in the lower panel. The two first thymidylic residues of the sequence of strand A probably correspond to the AT tail as indicated in the upper diagram.

The mRNA selected by hybridization to C56 cDNA immobilized on nitrocellulose filters, followed by elution from the films (as in Example 1) was translated in a reticulocyte lysate cell-free system and the [$^{35}$S]-methionine-labeled translation products were analyzed by polyacrylamide gel electrophoresis in Na-dodecyl sulfate according to the method described in Weissenbach et al. (1979) adapted from Laemle (1970). The C56 cDNA-selected RNA is translated into a 56,000-Mr protein. The sequence of the C56 cDNA permits one skilled in the art to deduce 65 amino acids of the carboxy terminal sequence of the 56,000 Mr protein (FIG. 4).

Figure 5A:
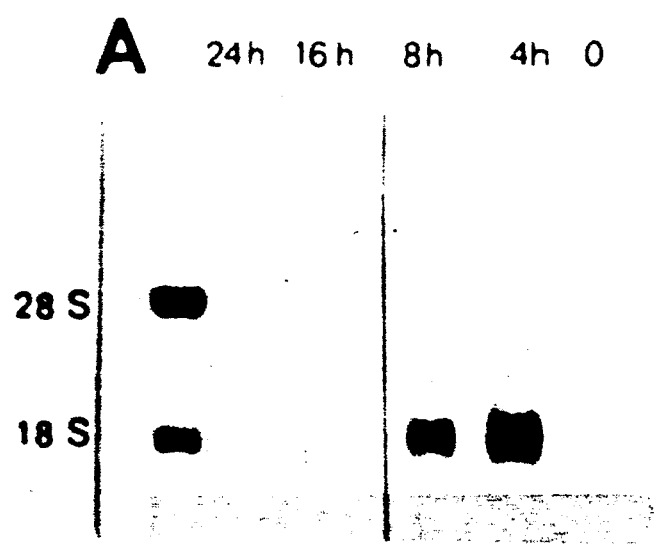
FIG 5A depicts Poly (A)+ RNA 7 micrograms from Namalva cells treated with IFN-alpha 1000 U/ml for the indicated times were electrophoresed on agarose gels and, after blotting, were hybridized with nick-translated [$^{32}$P]-C56 plasmid DNA.
Figure 5B:
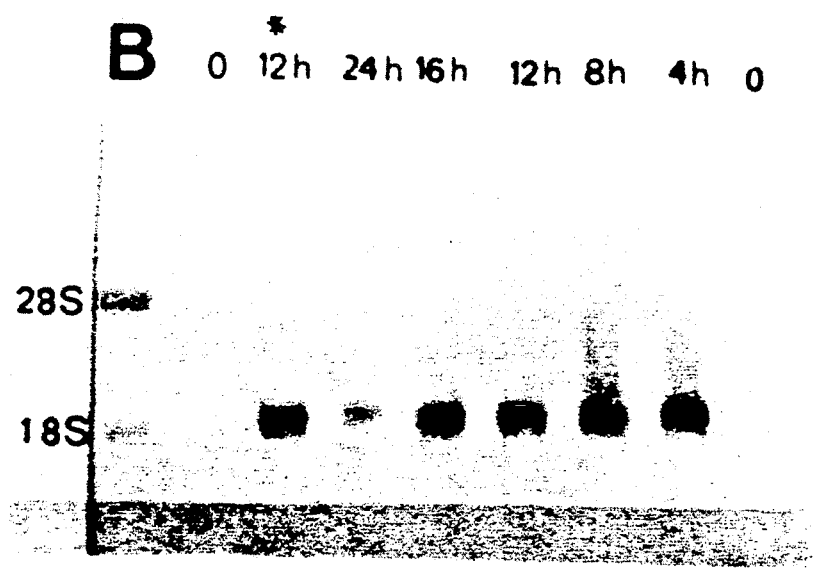
FIG. 5B depicts Poly (A)$^{30}$RNA, 7 micrograms from SV80 cells treated with 200 U/ml IFN-beta for the indicated times. The asterisk indicates an RNA sample from cells treated with IFN-beta-1 purified on monoclonal antibody column ($2 \times 10^8$ U/mg).
Figure 5C:
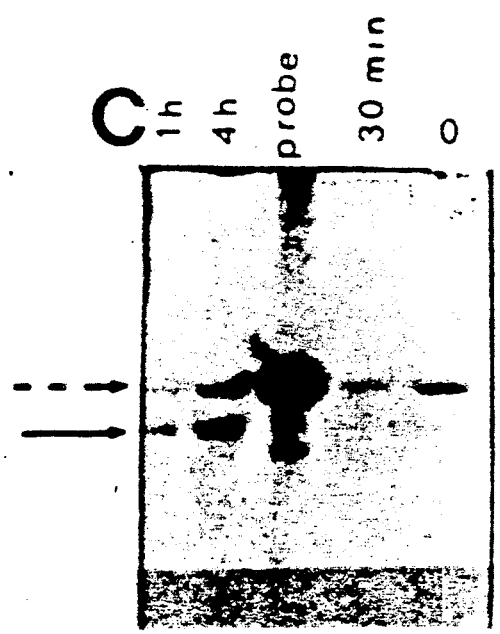
FIG. 5C depicts Poly (A)+RNA, 1 microgram, from SV80 cells treated as in (5B) was hybridized in liquid with 3' end-labeled fragment I of C56 DNA (see FIG. 4). The hybrids were treated with S$_1$-nuclease and analyzed on denaturing gels. The mRNA-hybridized probe (→) is shorter than the self-reassociated probe (→).

Hybridization of the C56 cDNA to RNA extracted from SV80 cells treated various times by interferon-beta (200 U per ml), shows that the C56 mRNA starts to appear at 1 hour after interferon addition (FIG. 5). The C56 RNA reaches its maximum after 4 hours, but is still detectable, although reduced, at 24 hours. Induction of C56 mRNA was also demonstrated in diploid fibroblasts, and in lymphoblastoid cells. Induction was proportional to the concentration of interferon between 10 and 200 units per ml. C56 mRNA was also induced by interferons alpha and gamma, although the latter was less efficient. The absence of this mRNA in non-treated cells and its strong and rapid increase after interferon addition make the C56 cDNA an excellent probe to evaluate the response of cells to interferon. The techniques described for E-cDNA in Example 1, can be similarly applied to the C56 cDNA.

The availability of a number of cDNA corresponding to mRNA induced by interferon offers new perspectives. In particular, interferon- is needed at 100-fold lower concentrations to induce HLA-A,B,C mRNA than to induced E-mRNA or C56 mRNA (Wallach et al. (1982); on the other hand, some subspecies of interferon-alpha, such as alpha-d can induce E-mRNA when a concentration 100 times lower than those needed to induce HLA-A,B,C mRNA. A comparison of the hybridization of different cloned cDNAs to the same RNA sample, can indicate what type of interferon is involved. Thus, more information can be derived from the comparison of different cDNA than from the use of only one cDNA probe.

EXAMPLE 3

A Kit For The Measure Of Interferon-Induced mRNAs

The Kit would provide the cloned cDNA specific for the mRNA of the (2'-5') oligo A synthetase and for the mRNA of the 56,000 Mr protein, described herein, as well as reagents to carry out the hybridization tests: comprising reagents for nick-translation with deoxyribonuclease I and -gamma-dCTP, [$^{32}$P]-gamma-dCTP, reagents for hybridization on nitrocellulose membranes, and reagents for RNA extraction from the cells.

EXAMPLE 4

Sequence of cDNA for the 1.6 kb (2'-5') oliqo A synthetase mRNA

Figure 6A:
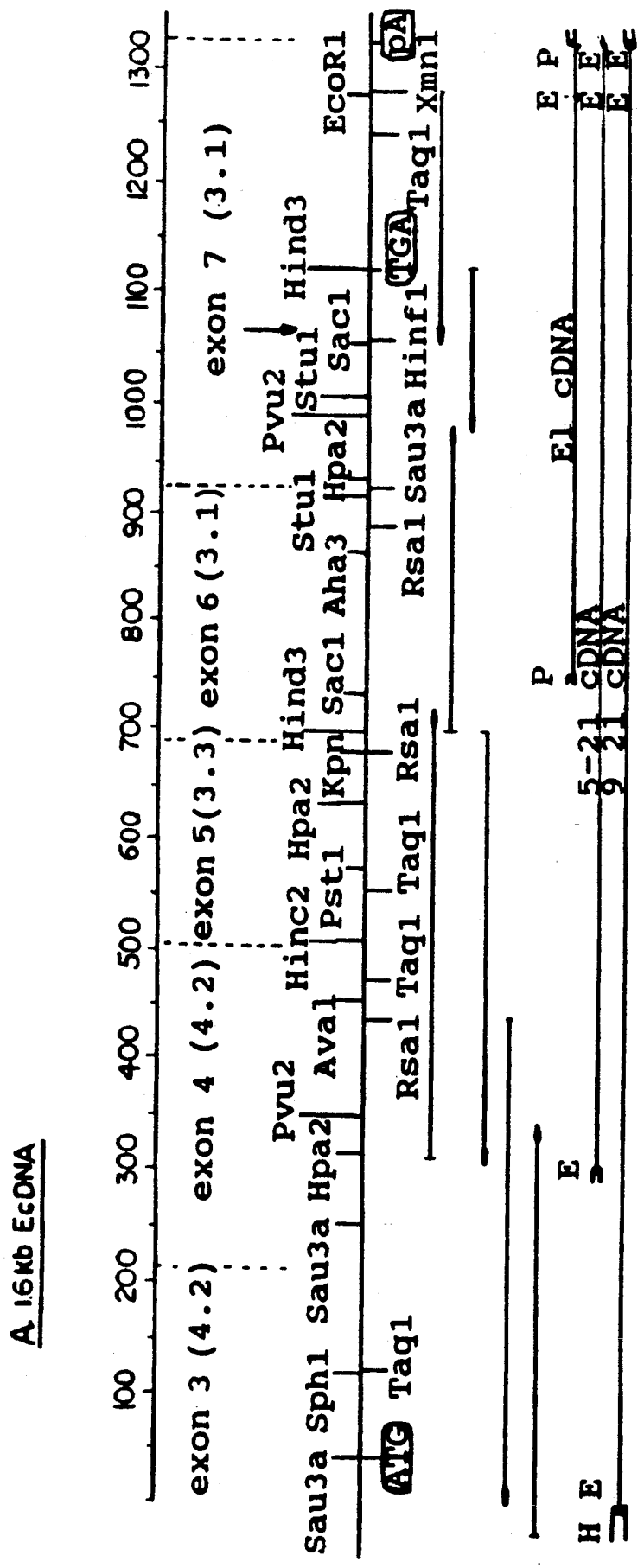
FIG. 6A depicts the map of the 1.6 kb cDNA. The position of the El cDNA (Merlin et al., 1983) and of the lambda gt 10 cDNAs is shown. pA is the polyadenylation site. The exon limits are shown by vertical dotted lines. The size of the genomic DNA fragments carrying each exon are given in parentheses. The vertical arrow shows the position of the additional splice site in the 1.8 kb RNA. The strategy for sequencing the 9-21 and 5-21 cDNAs is indicated. The sequence from the 3' EcoRl site (E) to the PstI site (P) was determined in the El cDNA (Merlin et al., 1983).

The partial $E_1$ cDNA clone (Merlin et al., 1983), shown to be the 3' end of the 1.6 kb (2'-5') oligo A synthetase by IFN in human cells (Benech et al, 1985) was used to screen a lambda gt10 cDNA library from SV80 cell RNA (Wolf and Rotter, 1985). By restriction mapping, clone lambda gt10 9-2 was found to contain the El cDNA at the 3' end of a 1.32 kb EcoRl insert (FIG. 6A) which was subcloned in pBR (9-21 cDNA). Sequencing was carried out as outlined in FIG. 6A and confirmed that the the 9-21 cDNA contains the C-terminus and 3' untranslated sequence previously reported for the $E_1$ cDNA (Merlin et al., 1983). The 9-21 cDNA sequence (FIG. 7) predicts an open reading frame of 364 amino acids starting at an AIGATG sequence. A computer program based on the 3-base periodicity of protein-coding sequences (Trifonov, 1984) indicated that the only compatible reading frame is the one starting from this ATGATG. It is possible that translation initiates at the second ATG in this site, since it is the only one preceded by an A at −3 and having homology with the concensus translation initiation sequence (Kozak, 1984).

Figure 12:
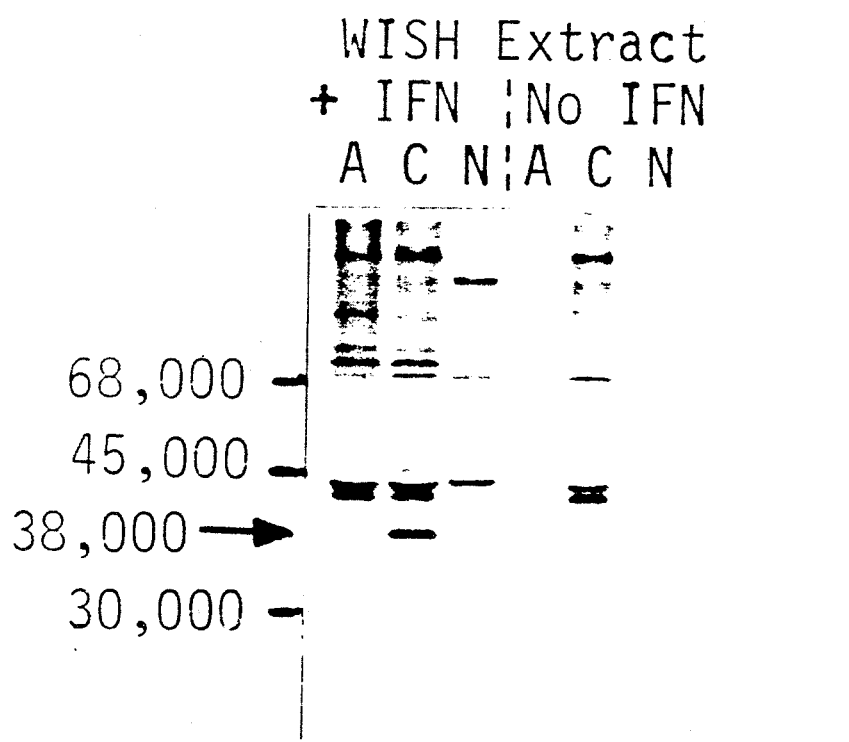
FIG. 12 depicts the SDS-acrylamide gel electrophoresis of $^{35}$S-methionine labeled proteins from IFN treated WISH cells immunoprecipitated by antiserum to synthetic peptides.

The enzyme thus coded by the 1.6 kb (2'-5') oligo A synthetase RNA has a molecular weight of about 41,700 daltons, based on the deduced amino acid sequence, which is in good agreement with the apparent 38,000 Mr protein seen by SDS-polyacrylamide gel electrophoresis of the in vitro translation product of RNA hybridized to $E_1$ cDNA (Merlin et al., 1983). The C-terminal heptadecapeptide predicted by the open reading frame, was synthesized chemically and used to immunize rabbits. The antiserum obtained (C in FIG. 12) precipitates specifically a protein migrating at 38,000-Mr in SDS gel electrophoresis from $^{35}$S-methionine labeled extracts of cells treated by IFN which is absent from untreated cells. Two experiments confirmed that this protein has (2'-5') oligo A synthetase activity: 1) it was removed from the extracts by passsage through a poly (rI)(rC) agarose column; and 2) the supernatant remaining after immunoprecipitation was depleted of a large part of the enzymatic activity.

EXAMPLE 5

Sequence of cDNA for the 1.8 kb (2'-5') oliqo A synthetase mRNA

Figure 6B:
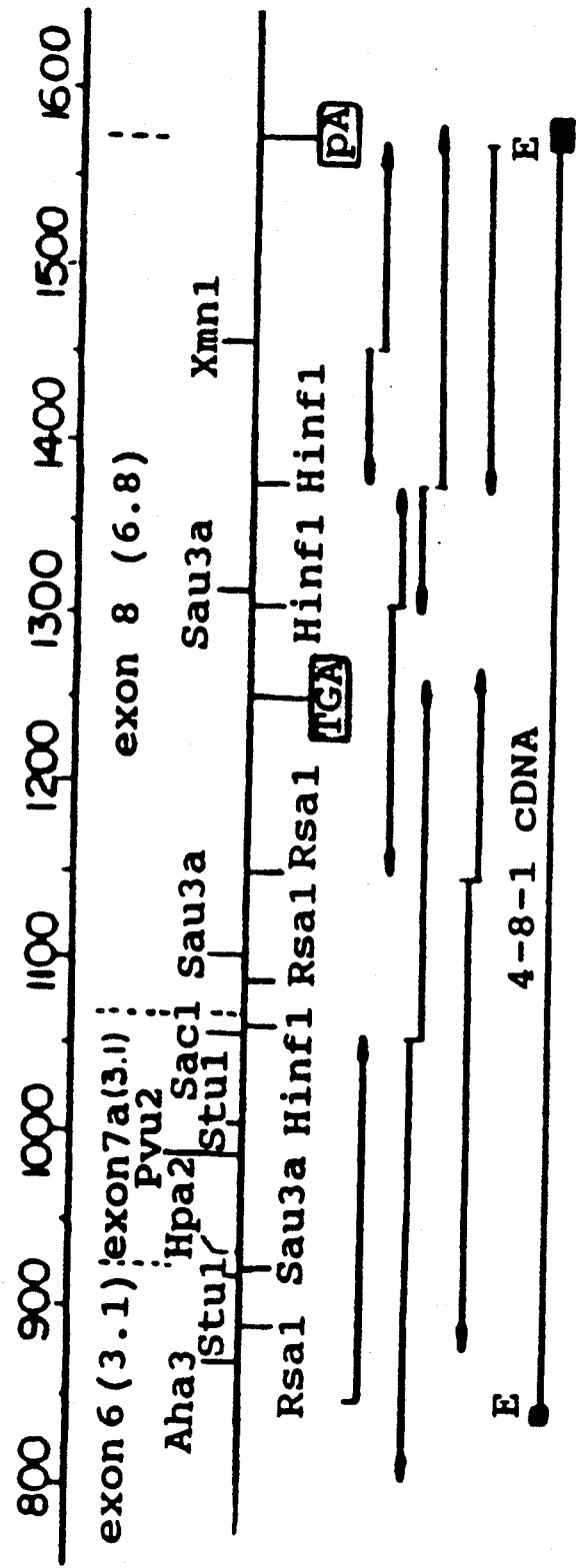

A genomic DNA fragment corresponding to the additional exon of the 1.8 kb RNA (Benech et al., 1985; see FIG. 9) was used as probe to isolate an E18 cDNA clone, 48-1, from the same lambda gt10 cDNA library of SV80 RNA. The restriction map of the E18 cDNA clone (FIG. 6B) confirmed that its 5' end is part of the E16 cDNA but that its 3' end differs. Sequencing (FIG. 7) revealed that the junction is at nucleotide 1071 of the E16 9-21 cDNA clone, the last 247 nucleotide of E16 being replaced by a 515 nucleotide-long sequence terminated by a different polyadenylation site. This difference accounts for the 0.2 kb difference in size between the two mRNAs seen on Northern blots. The 5' portion of the E18 cDNA shows no base change from the sequence of the E16 cDNA, but is incomplete. The gene mapping described below, indicates that both 1.6 and 1.8 kb mRNAs have the same 5' end.

Figure 8:
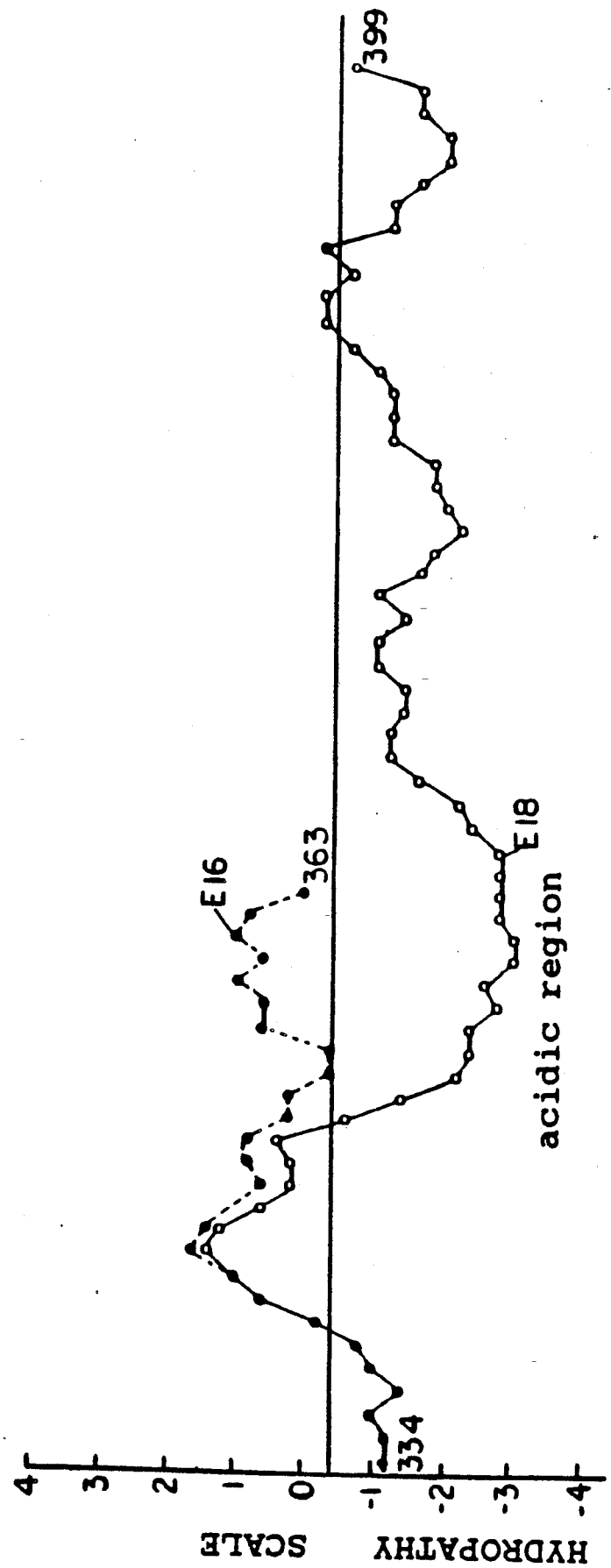
FIG. 8 depicts the hydropathy plot of the C-termini of the E16 and E18 (2'-5') oligo A synthetases. The computer program of Kyte and Doolittle (1982) was used. Hydrophobic regions are over the midline. The acidic region in E18 corresponds to amino acids 353 to 358 in FIG. 7.

The 3' region of the E18 cDNA which diverges from the E16 sequence, contains an open reading frame ending after 54 codons. This reading frame, which leaves a 50 nucleotide-long untranslated region, was confirmed by the computer program based on the 3 base periodicity of protein-coding sequences (Trifonov, 1984). An alternate longer open reading frame would not be in the same computed phrase as the 5' portion common with the E16 cDNA. A hydropathy plot (Kyte and Doolittle, 1982) on the prpredicted C-termini of the 1.6 and 1.8 kb mRNA protein products, indicates a striking difference between the two forms of the (2'-5') oligo A synthetase (FIG. 8). The C-terminus of the E16 protein is very hydrophobic, while that of the E18 protein is hydrophilic and contains two acidic regions (Asp-Asp-Glu-Thr-Asp-Asp and Glu-Glu-Asp) (FIG. 7). Furthermore, a possible glycosylation site is present in the C-terminus of the E18 product (FIG. 7).

Figure 13:
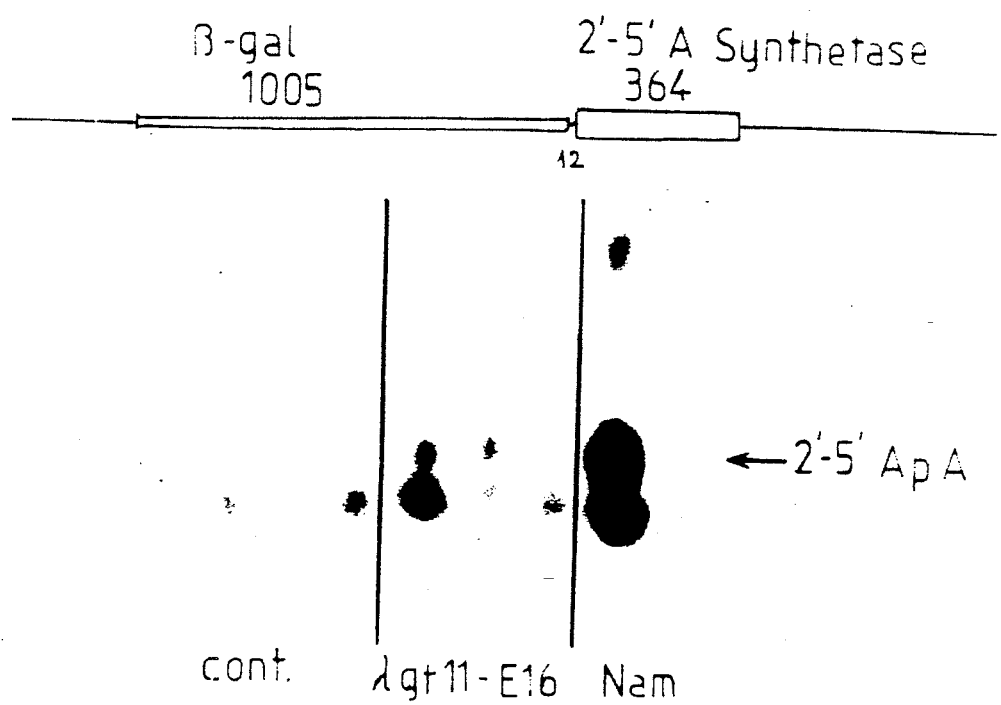
FIG. 13 depicts the expression of E16 cDNA in E. coli. Extracts of E. coli lysogen Agtll-E16 induced by IPTG at 42° C. wee assayed on poly (rI)(rC) agarose beads for (2'-5') oligo A synthesis. Con=extracts of E. coli with E16 cDNA in opposite orientation to lac Z gene. Nam=extracts of IFN-treated Namalva cells. Electrophroresis at pH 3.5 of alkaline phosphatased $^{32}$p-a-ATP labeled products are shown.

The 9-21 cDNA was subcloned in lambda-gt11 so as to fuse the coding frame in phase with the lac Z gene. Extracts of the *E. coli* lysogen containing this phase, showed clearly (2'-5') oligo A synthetase activity after binding to poly(rI)(rC) agarose, while no activity was found when the 9-21 cDNA had been fused in the opposite orientation (FIG. 13). This expression in *E. coli* demonstrates that the cDNA indeed corresponds to the structural gene coding for the ds RNA activated (2'-5') oligo A synthetase and that the protein of about 40 kd coded by the IFN induced RNA is the enzyme itself, and not a regulatory factor. This protein does not seem to require post-translational modifications to exhibit enzymatic activity.

The transformed cell containing the 9-21 cDNA has been designated *Escherichia coli* lambda-gt11-E16 and deposited under Accession No. I496 with the Collection National Cultures de Micro-organismes, Institut Pasteur, 25 rue du Docteur Roux, 75724-Paris-Cedex 15, France. This deposit was made pursuant to the Budapest Treaty On the International Recognition Of The Deposit Of Microorganisms For The Purposes Of Patent Procedure.

EXAMPLE 6

Organization of the human (2'-5') oligo A synthetase gene

Three overlapping genomic clones were isolated using the $E_1$ cDNA as probe (Benech et al., 1985), one from a library of partial EcoRl digest of human blood cell DNA (Mory et al., 1981) and two from a library of partial AluI and Hae3 digest of embryonic human DNA (Maniatis et al., 1978). The genomic clones represent about 29 kb of human DNA and no evidence for more than one E gene was found while screening the libraries. Southern blots of genomic DNA are consistent with the existence of a single gene (FIG. 9). By Northern blot analysis using genomic DNA fragments as probes, by S1 nuclease mapping and by sequencing, the E16 cDNA 9-21 was shown to correspond to five exons on the gene (FIG. 9). The ATGATG sequence is found in exon 3, while the termination codon and 3' untranslated region with the polyadenylation site of the 1.6 kb RNA are found in exon 7. The structure of the more 5' exons 1 and 2 is described below. The sequences of the intron-exon boundaries were determined (Table 2) and follow the CAG and GT rule for the splice acceptor and donor sites (Breathnach and Chambon, 1981).

A sequence CTGAC/T is commonly found not far from the splice acceptor, as reviewed recently by Keller (1984). It is notable that the CTGAC/T region shows base complementarity to the sequence of the intron-/exon 3' boundary (acceptor site; Table 2), in addition to the complementarity of the intron donor site with the CTGAC sequence pointed out by Keller (1984) as playing a role in the lariot model.

The sequences of the 5 exons containing the coding region of the (2'-5') oligo A synthetase produced by the 1.6 kb mRNA, indicates that the enzyme is composed of domains with differing amino acid compositions (Table 3}. The first exonic domain (60 amino acids) is rich in aspartic acid, in the second (amino acids 61 to 156) arginine is predominant, the next two exons (amino acids 157 to 218 and 219 to 295) are lysine rich, and the C-terminus of the E16 product (296 to 364) is very rich in proline and alanine.

TABLE 2
EXON-INTRON BOUNDARIES IN THE HUMAN (2'-5') OLIGO A SYNTHETASE GENE

```
                    (4.2)              -50
    ..CCCTTCTGAGGAAACGAAACCAACAG CAGTCCAAG....
                                 exon 3              (4.2)
                                 ..AAG.GTG.GTA.AAG GTGAGCGG....1.3 kb
                                                213

(4.2)..GGTTTGCCTTACTAAG   214
    CATCAATTATTATTTTTGTTCTTTTTTCAG GGT.GGC.TTC.TCA..
                                 exon 4              (4.2)
                                 ..GAT.GCC.CTG.G GTGAGAGCTC...2.3 kb
                                              502

(3.3)..GAAGAGCTGAC         503
    CCTAAGTTGTAAGTTTTACCCAGACAG GT.CAG.TTG.ACT..
                                 exon 5              (3.3)
                                 ..TGG.TAC.CAA.AAT GTATGGTTT....5.3 kb
                                              687

(3.1)..TGAGCAAACCAA        688
    TTTTTTTCTGATTGTTTTTCCTCTTCTCAG TGT.AAG.AAG.AAG..
                                 exon 6              (3.1)
                                 ..ACG.AAA.CCC.AG GTATGCTATCCCACATGGCTTG..0.9 kb
                                              916

(3.1)               -Pst 1- 917
    TACCTGTCCTCTCTAAATGCTGCTCTGCAG G.CCT.GTG.ATC..
                                 exon 7a             (3.1)         EcoR1-   (0.7)
                                 ..TGG.ATT.CTG.CTG GTGAGACCT....GAATTCATTCCCCTAAG
                                              1071  AGTAATAATAAATAATCTCTAACACCATTT
                                                    ATTGACTGTCTGCTTCGGGCTC..1.4 kb (6.8)        BamH1-                         (whole intron = 1.6 kb)
               ....GGATCCAG
    ATGGCATGTCACAGTATACTAAATGCTCAC
    T ATCCAGCTGCAATGCAGGAAGACTCCC   1072   exon 8 (1.8 KB RNA)          1585
    CTGATGTGATCATGTGTCTCACCCTTTCAG   GCT.GAA.AGC...AATAAAAATAAAGCAAATACCATTTATTGGGTG..
```

For exon numbering see FIGS. 7 and 9. The self-complementary regions between the CTGAT/C, or CTTAC, CTGTC (Keller, 1984) and splice acceptor CAG are underlined. The polyadenylation sites with a conserved undecanucleotide of the 1.6 and 1.8 kb RNAs (see FIG. 7) are underscored by dots.
The numbers in parentheses are the size of the EcoR1 genomic fragments carrying the introns or exons (see FIG. 9).
The start and end of each exon is numbered as in the 9-21 E cDNA of FIG. 7.

TABLE 3
EXONIC DOMAINS OF THE E16 AND E18 (2'-5') OLIGO A SYNTHETASES

| AA | 1-60 (60) | 61-156 (96) | 157-218 (62) | 219-295 (77) | 296-346 (51) | E16 C-term. 347-364 (18) | E18 C-term. 347-400 (54) |
|---|---|---|---|---|---|---|---|
| ALA | 2 (3.3) | 7 (7.3) | 0 (0.0) | 3 (3.9) | 4 (7.8) | 3 (16.7) | 4 (7.4) |
| ARG | 4 (6.7) | 10 (10.4) | 3 (4.8) | 5 (6.5) | 1 (2.0) | 1 (5.6) | 2 (3.7) |
| ASH | 1 (1.7) | 2 (2.1) | 2 (3.2) | 3 (3.9) | 3 (5.9) | 0 (0.0) | 1 (1.9) |
| ASP | 6 (10.0) | 5 (5.2) | 2 (3.2) | 1 (1.3) | 4 (7.8) | 0 (0.0) | 5 (9.3) |
| CYS | 4 (6.7) | 1 (1.0) | 2 (3.2) | 2 (2.6) | 1 (2.0) | 0 (0.0) | 1 (1.9) |
| GLN | 1 (1.7) | 7 (7.3) | 6 (9.7) | 5 (6.5) | 2 (3.9) | 0 (0.0) | 3 (5.6) |
| GLU | 2 (3.3) | 7 (7.3) | 5 (8.1) | 4 (5.2) | 2 (3.9) | 1 (5.6) | 5 (9.3) |
| GLY | 2 (3.3) | 9 (9.4) | 3 (4.8) | 3 (3.9) | 6 (11.8) | 0 (0.0) | 2 (3.7) |
| HIS | 1 (1.7) | 0 (0.0) | 1 (1.6) | 1 (1.3) | 0 (0.0) | 1 (5.6) | 3 (5.6) |
| ILE | 5 (8.3) | 2 (2.1) | 3 (4.8) | 4 (5.2) | 2 (3.9) | 1 (5.6) | 2 (3.7) |
| LEU | 5 (8.3) | 13 (13.5) | 8 (12.9) | 10 (13.0) | 6 (11.8) | 2 (11.1) | 2 (3.7) |
| LYS | 5 (8.3) | 2 (2.1) | 7 (11.3) | 9 (11.7) | 2 (3.9) | 0 (0.0) | 1 (1.9) |
| MET | 3 (5.0) | 0 (0.0) | 0 (0.0) | 1 (1.3) | 0 (0.0) | 0 (0.0) | 0 (0.0) |
| PHI | 4 (6.7) | 7 (7.3) | 3 (4.8) | 3 (3.9) | 1 (2.0) | 1 (5.6) | 1 (1.9) |
| PRO | 3 (5.0) | 4 (4.2) | 3 (4.8) | 4 (5.2) | 6 (11.8) | 5 (27.8) | 4 (7.4) |
| SER | 4 (6.7) | 8 (8.3) | 3 (4.8) | 1 (1.3) | 3 (5.9) | 2 (11.1) | 5 (9.3) |
| THR | 2 (3.3) | 4 (4.2) | 5 (8.1) | 6 (7.8) | 1 (2.0) | 0 (0.0) | 8 (14.8) |
| TRP | 0 (0.0) | 1 (1.0) | 1 (1.6) | 2 (2.6) | 4 (7.8) | 0 (0.0) | 1 (1.9) |
| TYR | 2 (3.3) | 0 (0.0) | 3 (4.8) | 7 (9.1) | 1 (2.0) | 0 (0.0) | 4 (7.4) |

TABLE 3-continued

EXONIC DOMAINS OF THE E16 AND E18 (2'-5') OLIGO A SYNTHETASES

| AA | 1-60 (60) | 61-156 (96) | 157-218 (62) | 219-295 (77) | 296-346 (51) | E16 C-term. 347-364 (18) | E18 C-term. 347-400 (54) |
|---|---|---|---|---|---|---|---|
| VAL | 4 (6.7) | 7 (7.3) | 2 (3.2) | 3 (3.9) | 2 (3.9) | 1 (5.6) | 0 (0.0) |

Although the E18 cDNA 48-1 is incomplete, we found that exons 1-6 (FIG. 9) hybridize to the 1.8 kb mRNA as well as to the 1.6 kb mRNA on Northern blots. The structure of the two RNAs is most likely identical up to exon 7. The additional splicing from the middle of exon 7 to exon 8 characterizing the E18 cDNA, was confirmed by sequencing these intron-exon boundaries in the genomic DNA clone (Table 2). The truncated exon 7a present in the E18 cDNA is followed by a 1.6 kb intron containing the polyadenylation site of the 1.6 kb RNA. Exon 8 begins 98 bp downstream from the unique BamHI site of the gene (Table 2, FIG. 9). The genomic exon 8 ends by the polyadenylation site of the 1.8 kb RNA, characterized by a tandem repeat of the AATAAA signal. Athough exon 7 and 8 have no homology, a conserved undecanucleotide ACCATT-TATTG, in which the third cytidine is polyadenylated, is present at the end of both exons (Table 2). As pointed out previously (Benech et al., 1985), a hairpin-loop structure can be formed in both cases between this conserved and undecanucelotide and the AATAAA region; such structures may participate in the cell-specific mechanism which determines whether cleavage and polyadenylation of the transcripts occur at the end of exon 7 or at the end of exon 8.

Based on the above gene mapping, the enzyme coded for by the 1.8 kb mRNA should be identical to the E16 product in the first 346 amino acids, which are followed by a specific 54 amino acid-long region, rich in aspartic acid, glutamic acid and threonine. The 400 amino acid-long E-18 enzyme would have a molecular weight of 46,000.

EXAMPLE 7

Figure 9A:
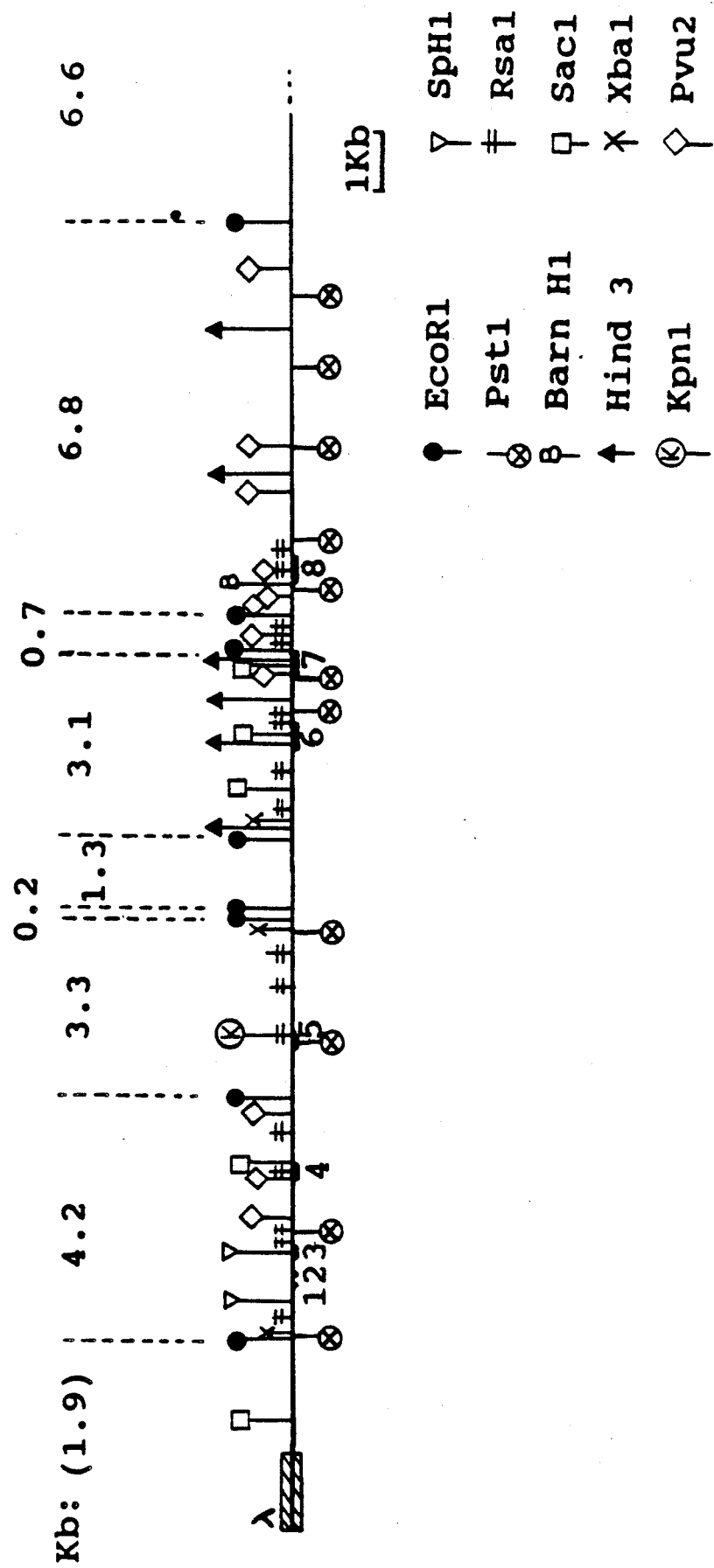
FIG. 9 depicts the restriction map of the human (2'-5') oligo A synthetase gene. A map constructed from three overlapping genomic clones is shown with the position of the 7 exons of the 1.6 kb RNA and the additional 8th exon of the 1.8 kb RNA (black bars). The insert shows a Southern blot of genomic DNA with the 48-1 cDNA as probe. Slot 1, Daudi DNA; slot 2, diploid fibroblast FS11 DNA.
Figure 9B:
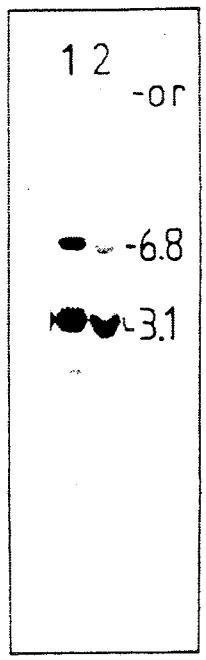

Two forms of the human (2'-5') oligo A synthetase produced by alternative splicing of the same gene Northern blot analysis of SV80 RNAs revealed that 3 species of RNA (1.6, 1.8 and 3.6 kb) hybridizing to E1 cDNA accumulate in cells up to 12 hours after exposure to IFN (Merlin et al., 1983). Additional unstable transcripts were also seen. The relationship between these RNAs was investigated by transcript mapping on genomic DNA clones. In two human genomic libraries, the E1 cDNA identified only one series of overlapping genomic DNA clones which represent 29 kb of human DNA (FIG. 9A) and were found to contain an apparently unique (2'-5') oligo A synthetase gene (Benech et al., 1985a). By S1 nuclease analysis and partial gene sequencing, the 9-21 (E1) cDNA was found to correspond to 5 exons (numbered 3-7 on FIG. 9A and in the sequence of FIG. 7). The 3' end and polyadenylation site of this cDNA was identified at the end of exon 7 (FIG. 9). However, hybridization of further downstream genomic DNA fragments to Northern blots of SV80 RNA, revealed (Benech et al., 1985) that only the 1.6 kb RNA ended at the polyadenylation site in exon 7, while both the 1.8 and 3 6 kb RNAs hybridized to an additional exon located 1.6 kb downstream and which ends also by a polyadenylation site (exon 8, FIG. 9).

Thus the 9-21 (E1) cDNA represents the 1.6 kb RNA and was renamed E16 cDNA. It was further found that the 3' half of exon 7 does not hybridize to the 1.8 kb RNA indicating that the transcript is formed by a splicing event from the middle of exon 7 to exon 8. All the 5' upstream exons hybridized to both 1.6 and 1.8 kb RNAs, indicating that the 2 RNAs differ only in their 3' ends. This was confirmed by the isolation from the SV80 lambda-gt10 cDNA library of a cDNA clone for the 1.8 kb RNA (clone 48-1 or E18 cDNA, FIG. 7B), which demonstrated the differential splicing and ended at the polyadenylation site of exon 8 (FIG. 9). A similar cDNA clone was found in a Daudi cDNA library by Saunders and Williams (1984). The E18 sequence locks the last 247 nucleotides of E16 which are replaced by 515 nucleotides accounting for the difference in size between the 1.6 and 1.8 kb RNAs.

The 1.8 kb RNA would thus code for a 46.000 Mr protein (E18) which differs from the E16 protein in its C-terminus. Like the E16 protein, the E18 product has ds RNA binding and (2'-5') oligo A synthetase activity as shown by translation of mRNA selected by hybridization to E18-specific DNA fragments (Benech et al., 1985). This suggests that the first 346 aminoacids common to the 2 proteins contain the catalytic sites. Examining the exon composition this common part appears composed of a N-terminal acidic domain, followed by three basic regions. The last 18 residues of the E16 protein form a very hydrophobic domain, which is replaced in E18 by a longer hydrophilic and acidic region which also contains a potential glycosylation site. This difference between the 2 enzymes may determine their ability to dimerize, or interact with other proteins and cellular structures. For example, E16 may bind to membranes while E18 may interact with basic proteins in ribosomes or in the nucleus.

Two forms of the (2'-5') oligo A synthetase were found by gel filtration in extracts of IFN-treated human cells (Revel et al., 1982): a 30-40 kd enzyme which could correspond to a monomeric form of the E16 or E18 proteins, and a 60-80 kd enzyme which remains to be identified. The 3.6 kb RNA does not seem to code for a large enzyme since transcript mapping showed that this RNA contains intronic regions (e.g. between exon 7 and which are removed from the 1.8 kb RNA and have no open reading frame We also failed to see large E mRNA in oocyte translations. An 80 kd protein in SDS was reported in purified human (HeLa) synthetase (Yand et al., 1981) but is enzymatic activity was not demonstrated. In enzyme purified from Namalava and CML cells (Revel et al , 1981b) we could detect a 40 kd band in SDS. Thus it remains possible that the 60-80 kd enzyme form is a dimer of the 40 kd protein. The human synthetase may differ from that in mouse cells where a large 3.8 kb RNA was seen under denaturing conditions which codes for a 80 kd enzyme (mainly cytoplasmic), in addition to a 1.5 kb RNA coding for a 30 kd enzyme (mainly nuclear) (St. Laurent et al., 1983). The human E cDNA detects a 3.8-4 kb and a 1.6-1.7 kb RNA in mouse cells, the large RNA hybridizing to E18-specific DNA (Mallucci et al., 1985). It is possible that in human cells the large RNA is further processed into 1.8 kb RNA, which has not been seen in mouse cells. Shulman et al. (1984) have used the fact that the bulk of the (2'-5') oligo A synthetase in human cells behaves as a smaller protein than in mouse cells to map the human synthetase gene to chromosome 11 in human rodent-hybrid cells. Antisera specific to E16 and E18 will help to elucidate the relationship between these proteins and the two forms of the native enzyme seen in human cells.

EXAMPLE 8

Cell specific expression of the two (2'-5') oligo A synthetase mRNAs

RNA from a number of human cell lines have been examined in Northern blots with the E cDNA probe (Merlin et al., 1983; Benech et al., 1985). Table 4 shows that human cells can be grouped in 3 classes according to the predominant E mRNA species induced by IFN. Lymphoblastoid B cell lines from Burkitt lymphomas have mainly the 1.8 kb RNA. Instead, several cell ines have the 1.6 and 3.6 kb RNA but little 1.8 kb RNA. If the 3.6 kb RNA is a partially spliced precursor of the 1.8 kb RNA, these cells may have an inhibition in the processing of the 3.6 kb RNA. T-lymphocyte lines (CEMT from an acute leukemia and Gash from hairy cell leukemia) contain like fibroplastic cells, all 3 E RNA species. The E18 polyadenylation (pA) site seems, therefore, to be used in all human cells to produce either 3.6 or 1.8 kb RNA. The E16 pA site seems not to be used in B lymphoblastoid cells. A conserved undecanucleotide present in both E16 and E18 pA sites (FIG. 9B) can form a hairpin-loop with the AATAAA signal and could have a role in site selection (Benech et al., 1985). E18 has a tandem repeat of the AATAAA signal (FIG. 9B) and could be a stronger pA site. Transcripts ending at the E18 pA site accumulate earlier after IFN addition than the 1.6 kb RNA (Benech et al., 1985).

TABLE 4
PREDOMINANT (2'-5') OLIGO A SYNTHETASE RNA SPECIES

| 3.6 kb | | 3.6 kb |
| --- | --- | --- |
| | 1.8 kb | 1.8 kb |
| 1.6 kb | | 1.6 kb |
| | B lymphoblastoid | |
| Histiocytic | Burkitt lymphoma: | Fibroblastic: |
| lymphoma U937 | - Daudi | - SV 80 |
| | - Namalva | - FS11 |
| Amniotic Wish | - Raji | |
| Cervix Ca HeLa | | T cells: |
| Raji × HeLa hybrids | | -CEMT |
| | | Hairy cell-leuk.: |
| | | -Gash |

The type of synthetase predominantly made may vary in different human cells. We found no correlation between the cytoplasmic or nuclear localization of the synthetase and the type of RNA present in the cells. However, Namalava cells seemed to have mainly the 30–40 kd enzyme upon gel filtration while HeLa and SV80 cells had also the 60–80 kd form (Revel et al., 1982).

EXAMPLE 9

Promoter region of the (2'-5') oligo A synthetase gene

Figure 10:
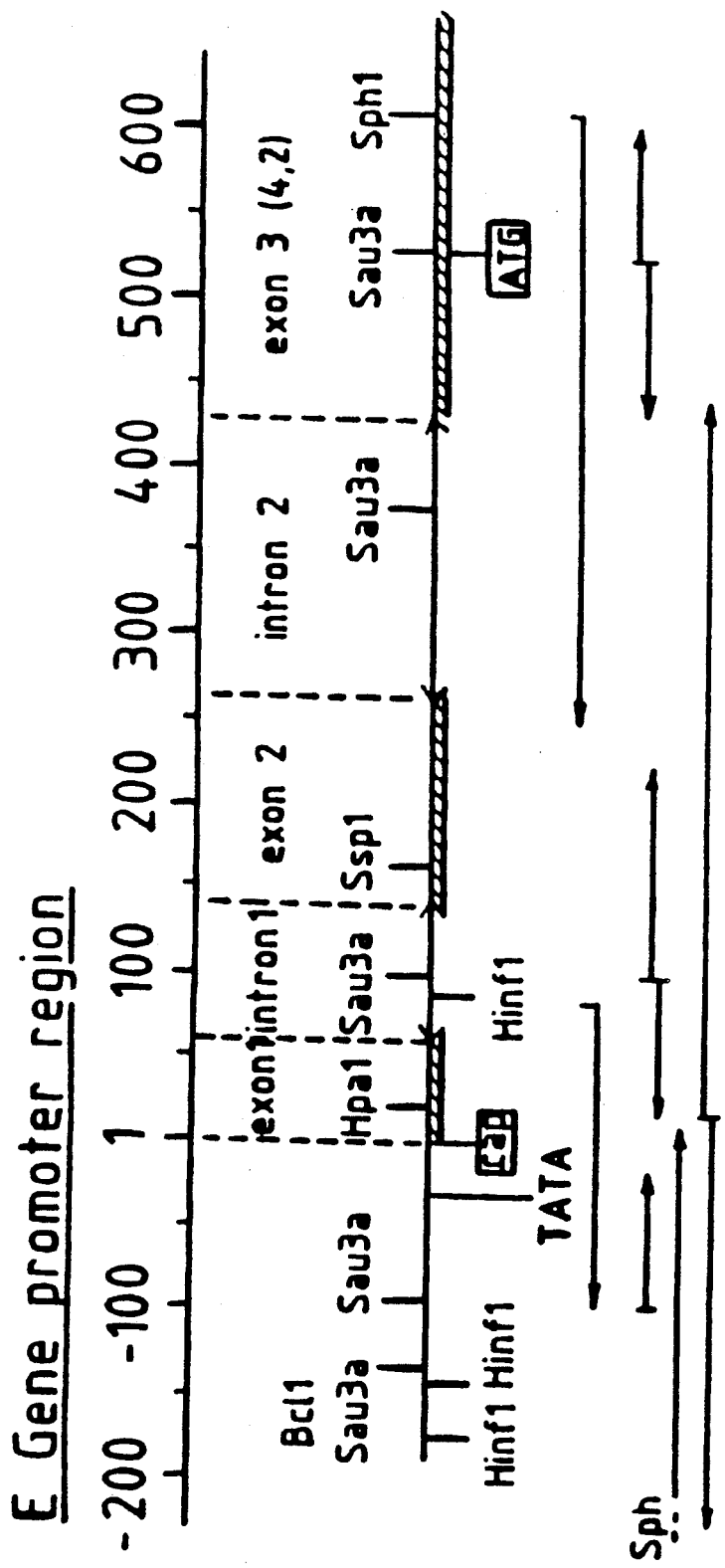
FIG. 10 depicts the promoter region of the human (2'-5') oligo A synthetase gene. A restriction map of the Sphl-Sphl 0.85 kb fragment from the 4.2 kb EcoRl genomic DNA segment in FIG. 9 is shown. The 5' end of the mRNAs is marked as cap.

The SphI-SohI fragment of 0.85 kb (FIG. 10) from the genomic 4.2 kb EcoRl fragment (FIG. 9) which contains part of exon 3 of the E16 cDNA 9-21 clone, hybridized in Northern blots with the 1.6, 1.8, 2.7 and 3.6 kb RNAs. However, upstream regions did not. Several experiments allowed to localize the RNA transcriptional start in this fragment. S1 nuclease analysis first showed that exon 3 starts about 50 nucleotides upstream of the end of the 9-21 cDNA. A primer extension experiment using an oligonucleotide from the end of the 9-21 cDNA, indicated that the 5' end of the mRNA is about 230 nucleotides from the 5' end of this cDNA. RNA hybridization with riboprobes produced in SP6 (Green et al., 1983) and RNAse digestion indicated two exons of 70 and 110 nucleotides preceding exon 3. By Sl nuclease analysis using a probe labeled at the unique HpaI site (FIG. 9), the 5' end of the mRNA was finally located 17 nucleotides upstream from the HpaI site. The sequence of this region is shown in FIG. 11. The location of the transcription initiation site 17 residues before the HpaI site, is supported by the presence of a TATAA box at position $-30$. A striking feature of the upstream sequences, is the high purine content (69.6%) mostly adenine (58.9%). Run of a homology matrix with other known promoter upstream sequences revealed a surprising homology with the human IFN promoters in particular with the sequence of the IFN-beta-1 gene promoter (Degrave et al., 1981). The purine-rich region from $-75$ to $-85$ of the IFN-beta-1 promoter, which contains the essential transcription signal described by Zinn et al., (1983), shows 90% homology with the region of the presumed promoter of the (2'-5') oligo A synthetase just upstream of the TATAA box ($-40$ to $-50$) (FIG. 11). This purine-rich signal is repeated in the IFN-beta-1 promoter in the segment between the TATAA box and the cap site; in this region, which may also have regulatory functions (Nir et al., 1984) the homology between the IFN-beta-1 gene and the (2'-5') oligo A synthetase gene is high. In contrast, search for homology with promoters of other genes, such as HLA genes (Malissen et al., 1982; Schamboeck et al., 1983) and the metallothionein II gene (Karin and Richards, 1982) which are activated by IFNs (Fellous et al., 1982; Rosa et al., 1983b; Friedman et al., 1984) showed no apparent sequence relationship in this region of the (2'-5') oligo A synthetase gene promoter. Also, no significant homology was seen with the body of the IFN-beta-1 gene.

The 5' untranslated leader of the (2'-5') oligo A synthetase mRNA (exon 1, 2 and part of exon 3) contains two short introns whose positions were tentatively determined by Sl analysis as shown in FIG. 11. The entire human (2'-5') oligo A synthetase gene is about 13 kb (FIG. 9) and the sum of the exons agrees with the observed sizes of the mRNAs.

EXAMPLE 10

Lambda GT10 cDNA clones of the (2'-5') oligo A synthetase

A lambda-gt10 cDNA library prepared from poly A+ RNA of human SV80 cells (Wolf and Rotter, 1985) was screened using as probe the PstI-PstI insert of the El cDNA plasmid described previously (Merlin et al., 1983). The insert corresponding to the 3' end of the 1.6 kb E RNA (Benech et al., 1985), was purified by agarose gel electrophoresis and nick-translated (Rigby et al., 1977). Plaques were repeatedly picked from 9cm plates ($10^5$ phages), and small scale lambda-DNA preparations were analyzed by restriction mapping by routine procedures (Maniatis et al., 1982). Fifteen lambda-gt10 cDNA clones containing the E1 cDNA fragment were isolated and phages 9-2 and 5-2 with the longest inserts were cut by EcoRl and the inserts subcloned into pBR322 to obtain E16 cDNA clones 9-21 and 5-21 of FIG. 6A. The same library was rescreened with a human genomic PstI-PstI 0.9 kb fragment from phage lambda-chEl (Benech et al., 1985), a fragment which specifically hybridizes to the 1.8 kb RNA. We thereby isolated lambda-gt10 cDNA clone 48-1 of FIG. 6B, along with another cDNA clone representing a partially spliced E RNA. Sequencing was carried out according to Maxam and Gilbert (1980). Restriction enzymes were from New England Biolabs and Boehringer. Homology matrix and hydropathy plot computer programs of Pustell and Kafatos (1982a,b) were run on an IBM PC. Three base periodicity to locate protein coding frames was computed according to Trifonov (1984).

EXAMPLE 11

Genomic DNA clones containing the (2'-5') oligo A synthetase gene

Three overlapping genomic clones were isolated as previously described (Benech et al., 1985): lambda-chEl from a partial EcoRl-cut DNA library (Mory et al., 1981) and lambda-chE2 and E3 from a partial AluI/Hae 3 DNA library (Maniatis et al., 1978). The genomic EcoRl fragments of these phages were subcloned in pBR322. Exon mapping was done: 1) by Southern blot hybridization of restriction digests from subcloned genomic fragments to various cDNA probes; 2) by hybridization of genomic DNA restriction fragments to Northern blots of poly A+ RNA from IFN-treated and untreated cells as described (Benech et al., 1985); and 3) by sequencing of intron-exon boundaries in comparison to cDNA. The internal SohI-SphI 0.87 kb segment of the genomic 4.2 kb EcoRl fragment containing the 5' end of the mRNA, was subcloned in the SohI site of pBR322 before sequencing. Primer extensions using synthetic oligodeoxyribonucleotides of 18-20 bases complementary to the mRNA (gift of Dr. D. Segev, InterYeda) were done as before (Rosa et al., 1983a). Riboprobe synthesis after subcloning in the SP6 vector was carried out according to instructions of Promega Biotec. DNA from Daudi lymphoblastoid cells and from FSll foreskin fibroblasts was prepared according to Wigler et al. (1979) and Southern blot analysis was done on Gene-Screen Plus nylon fiber sheets using hybridization procedure B recommended by the manufacturer (New England Nuclear).

EXAMPLE 12

Quick cell blot assay of (2'-5') oligo A synthetase RNAs for the clinical monitoring of IFN action The usefulness of measuring the (2'-5') oligo A synthetase has been shown in human peripheral blood mononuclear cells (PBMC) to monitor the response of patients to IFN-beta (Schattner et al., 1981a) and IFN-beta i.m. injections (Schoenfeld et al., 1984). Since the enzyme level of PBMC in normal healthy individuals is rather constant, this assay has allowed the diagnosis of viral infections evidenced by an increase in the enzyme in the PBMC and granulocytes (Schattner et al., 1981b; 1984; Schoenfeld et al., 1985). Decrease in the enzyme characterize acute leukemias with numerous blast cells (Wallach et al., 1982; Schattner et al., 1982). This technique has also been pioneered by Williams et al. (1981) and is now in wide use.

Synthetase E is strongly induced in cells treated by all three types of IFNs, alpha, beta and gamma, and its increase is a good marker of IFN activity (Wallach et al., 1982). It is therefore possible to use measurements of E levels to determine whether cells in vitro or in vivo have been exposed to IFN and respond to it. This measurement may be used as an assay for IFN in unknown solutions, by exposing cells to said solutions and determining the increase in E levels (Revel et al., U.S. Pat. No. 4,302,533). The measurement may also be used to establish whether IFN is produced in increased amounts in whole organisms including man.

The (2'-5') oligo A synthetase increases during differentiation of hematopoietic cells as a result of autocrine secretion of IFN-beta (Yarden et al., 1984). Another important application of E measurements is in the monitoring of patients under IFN therapy. Besides clinical changes, it is possible to establish that the patients respond to IFN by measuring the PBMC E level which increases 5-10 fold during systemic IFN-alpha as well as beta treatment (Schattner et al., 1981a; Schoenfeld et al., 1984). It is clear that assay of other IFN-induced activities or molecules may be used as well as the assay of the E enzyme, but this method has been the most widely used (Williams et al., Borden).

Figure 14:
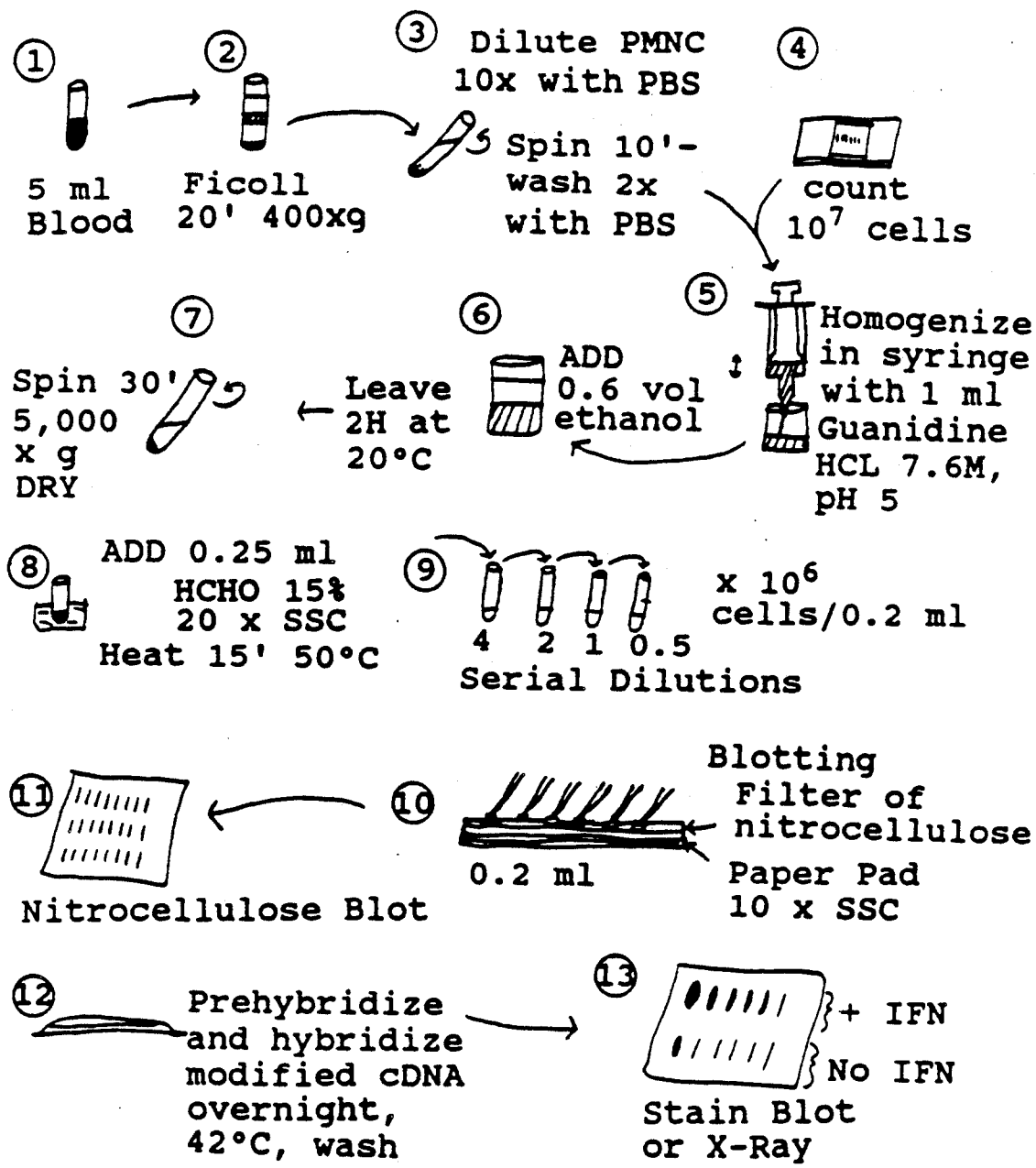
FIG. 14 depicts the rapid method for assay of (2'-5') oligo A synthetase RNAs in human peripheral white blood cells.
Figure 15:
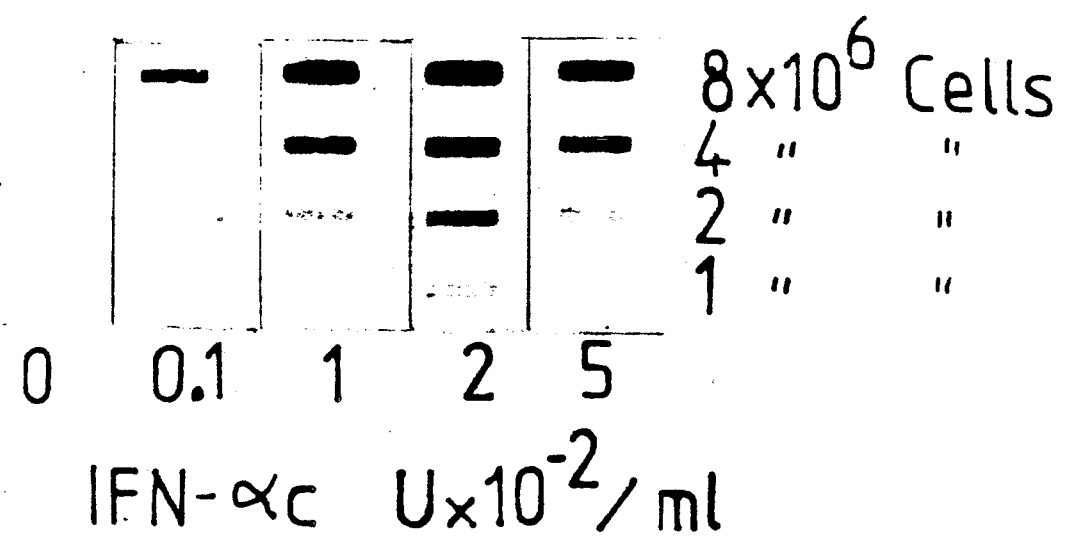
FIG. 15 depicts the quick cell blot for (2'-5') oligo A synthetase E RNAs in human PBMC according to the method of FIG. 14. Indicated number of cells and IFN (16 H treatment) were used. Autoradiography with $^{32}$P-cDNA.

Now the assay of E RNA in human PBMC is used for the same purpose. A quick cell blot (Cheley and Anderson, 1984) using the 9-21 E cDNA as probe was developed for PBMC (FIG. 14). Oligonucleotides derived from the E cDNA may also be used as probes. The effect of 10 U/ml IFN can easily be detected by this method (FIG. 15). Positive signals were obtained in a patient treated by $10^7$ units/day of IFN-alpha-c.

EXAMPLE 13

Immunoprecipitation of the (2'-5') oligo A synthetase activity by anti-(2'-5') oligo A synthetase peptide antibodies Antiserum B was raised against a peptide common to the E16 and the E18 sequences, while antiserum C was raised against a peptide found only in E16. We used these antibodies to verify that they immunoprecipitate the (2'-5') oligo A synthetase activity specifically. The (2'-5') oligo A synthetase activity adsorbed on the immune IgG-Protein A Sepharose and that remaining in the supernatant were compared to the same fractions obtained by using non-immune IgG. Extracts from two cell lines which express preferentially either the 1.6 kb RNA (Wish cells) or the 1.8 kb RNA (Daudi cells) (Benech, et al., 1985a) were compared. Antibodies C (E16-specific) were 20 times more efficient to adsorb the activity from Wish cells than normal serum. Substracting the background with normal serum, allows to evaluate what is specifically bound to anti-B and anti-C (FIG. 16). Anti-C retained the (2'-5') oligo A synthetase activity from Wish cells but not from Daudi cells, in the line with the absence of E16 mRNA and 40 kd protein in these cells (see Example 14). Anti-B adsorbed (2'-5') oligo A synthetase activity from both Daudi and Wish cell extracts.

The antibodies produced against peptides deducted from the cloned cDNAs, recognized, therefore, specifically different (2'-5') oligo A synthetase forms.

EXAMPLE 14

Figure 17:
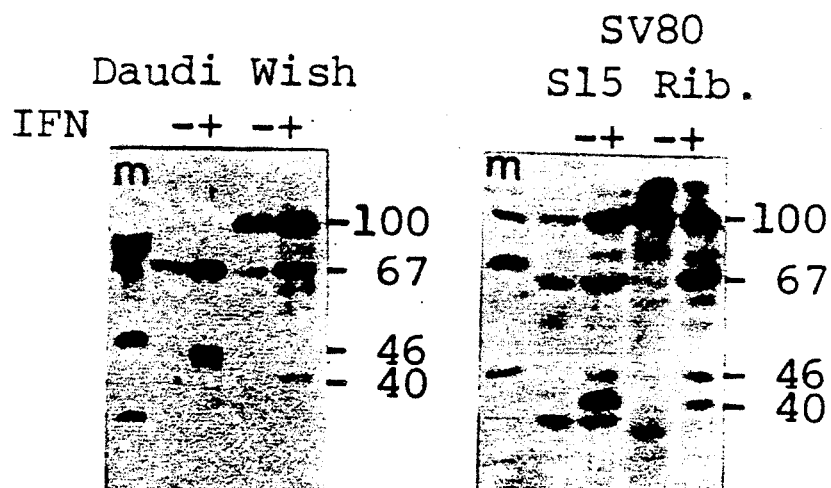
FIG. 17 depicts the electrophoresis and immuno-blotting of extracts from human cells as described in Example 14. The position of the 4 forms of (2'-5') oligo A synthetase is indicated by the numbers on the right of each blot. m=$^{14}$C-protein molecular weight markers. IFN treatment is indicated by +.

A) Immunoblot analysis of the different forms of (2'-5') oligo A synthetase from human cells The antibodies against peptide B were tested for their ability to bind specifically to (2'-5') oligo A synthetase in crude extracts of human cells separated by sodium-dodecyl-sulphate-polyacrylamide gel electrophoresis and blotted electrophoretically onto nitrocellulose paper. In additional to being recognized by the antibodies in immunoblots, we expect genuine (2'-5') oligo A synthetase proteins present in extracts of these human cells to be induced by IFN treatment, and we therefore looked only at the induced proteins revealed by the immunoblots (FIG. 17).

The cell line Daudi, Wish and SV80 were compared because of their differences in the pattern of expression of the (2'-5') oligo A synthetase mRNAs (see Example 13). Antibodies B detect as expected a 45-46 kd protein similar in size to the E18 product in Daudi cells and no 40 kd which would correspond to E16 whose mRNA is not expressed by Daudi cells. In contrast, the 40 kd E16 protein is present in Wish cells without 46 kd E18 in line with the absence of 1.8 kb RNA in these cells. Both proteins are detected by anti-B in SV80 cells. These results demonstrate that human cells produce the 40 and 46 kd proteins and this only when they express the 1.6 and 1.8 kb RNAs respectively.

Figure 18:
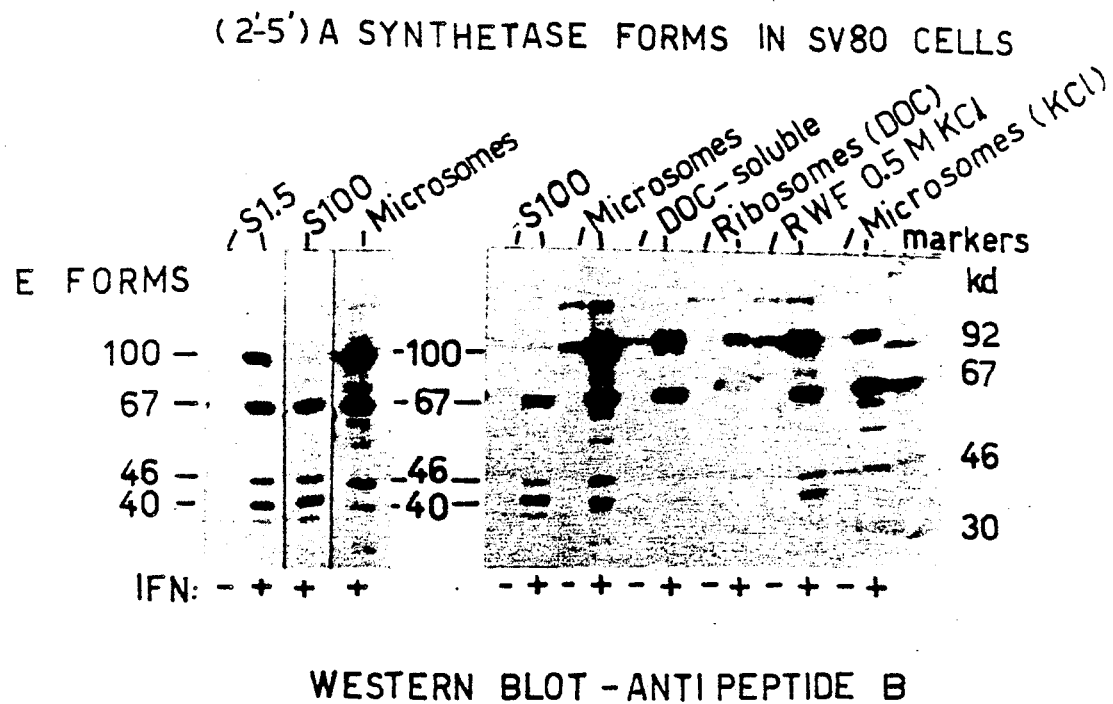
FIG. 18 depicts electrophoretic immunoblots of extracts from human SV80 cells with anti-(2'-5') oligo A synthetase peptide B. Left: crude cytoplasmic extract (S1.5), cell sap (S100) and microsomes (P100). Right: Na deoxycholate 10% extract of microsomes (DOC-soluble), high salt wash of microsomes (RWF) and microsomal pellet after salt extraction (Microsomes-KCl).

The immunoblots with anti-B also reveal that there are not only two forms of (2'-5') oligo A synthetase in human cells but probably four different forms. This can be deduced from the fact that in addition to the 40 and 46 kd proteins, anti-B clearly detected two other proteins of 100 kd and 67 kd which are induced by IFN (FIGS. 17 and 18). The 100 kd was not detected in Daudi cells, showing that the large proteins detected by anti-B are also expressed in a cell-specific pattern. The fact that the anti-B was raised against a peptide derived from the sequence of geniune (2'-5') oligo A synthetase forms, and that the two larger proteins are induced by IFN, makes it very likely that they belong to the (2'-5') oligo A synthetase system. To ascertain that these are (2'-5') oligo A synthetase forms, we have purified (2'-5') oligo A synthetase activity from different cellular fractions of SV80 and followed in parallel the protein detected by antibodies B.

B) Separation of the different active forms of (2'-5') oligo A synthetase

Figure 19:
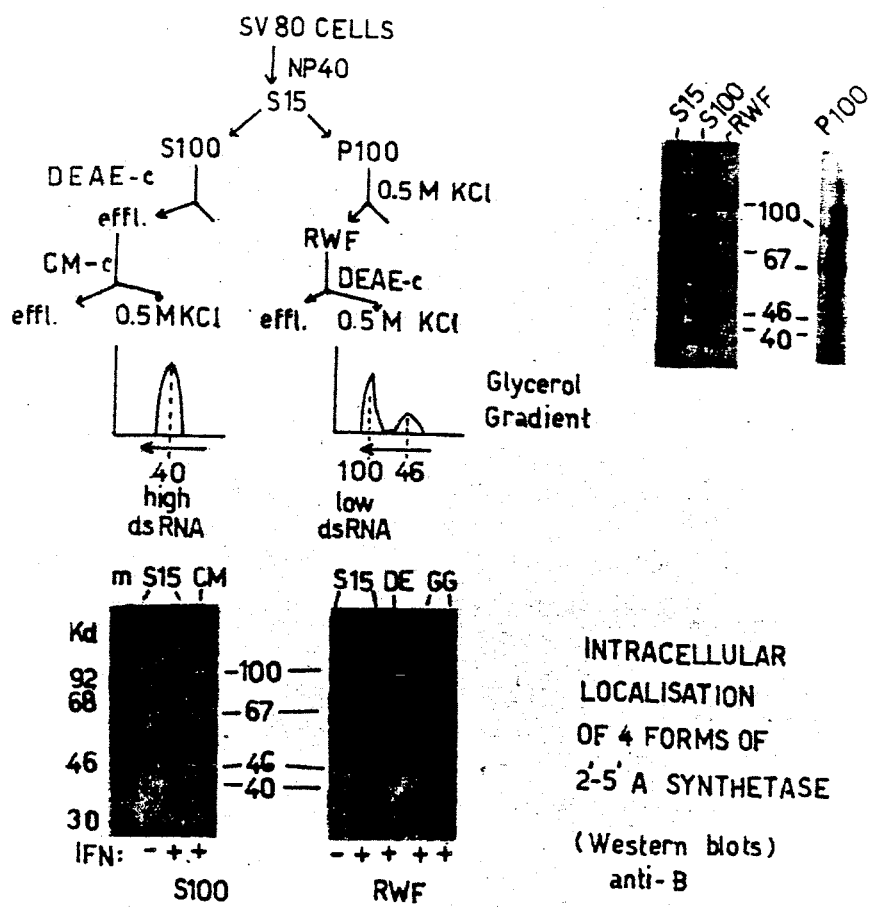
FIG. 19 depicts the fractionation of·S100 and high-salt wash of microsomes (RWF) on DEAE-cellulose and carboxymethyl-cellulose, followed by glycerol gradient. The (2'-5') oligo A synthetase profile and protein detected by anti-B are shown below the gradients. Electrophoretic immunoblot shows fraction CM (CM-cellulose eluate from the S100 proteins non absorbed to DEAE-cellulose) on the left blot. On the right-hand blot fraction DE (DEAE-cellulose eluate of RWF) and fraction GG (heavy peak of 80-100 kd from glycerol gradient of fraction DE).

The separation of the different protein species detected by antibodies B is shown in FIGS. 18 and 19. Most of the 40 kd protein remains in the 100,00g supernant (S100) of NP40 cytoplasmic extracts from SV80 cells. It is not adsorbed on DEAE-cellulose in low salt and adsorbs to CM-cellulose from which it elutes at high salt concentration. In contrast, the 100 kd protein is almost absent from S100 and is concentrated in the microsomal pellet (P100) from which it can be solubilized by sodium deoxycholate (DOC) or 0.5M KCl. This protein was adsorbed on DEAE-cellulose at low salt and elutes at high salt. The 67 kd and 45-46 kd remain partly in S100 but are relatively concentrated per mg protein in the microsomal pellet. They appear to be less readily extractable from microsomes by DOC or KCl. Sedimentation on glycerol 9radients showed that the activity purified from S100 after CM-cellulose parallels the sedimentation of the 40 kd protein E16 The fraction purified from P100 and eluted from DEAE-cellulose, containing the 100 and 46 kd proteins, separated into two peaks on glycerol gradients, sedimenting as 80,000 and 45,000 Mr proteins The (2'-5') oligo A synthetase activity in the heavy peak parallels the presence of the 100 kd protein

Figure 20:
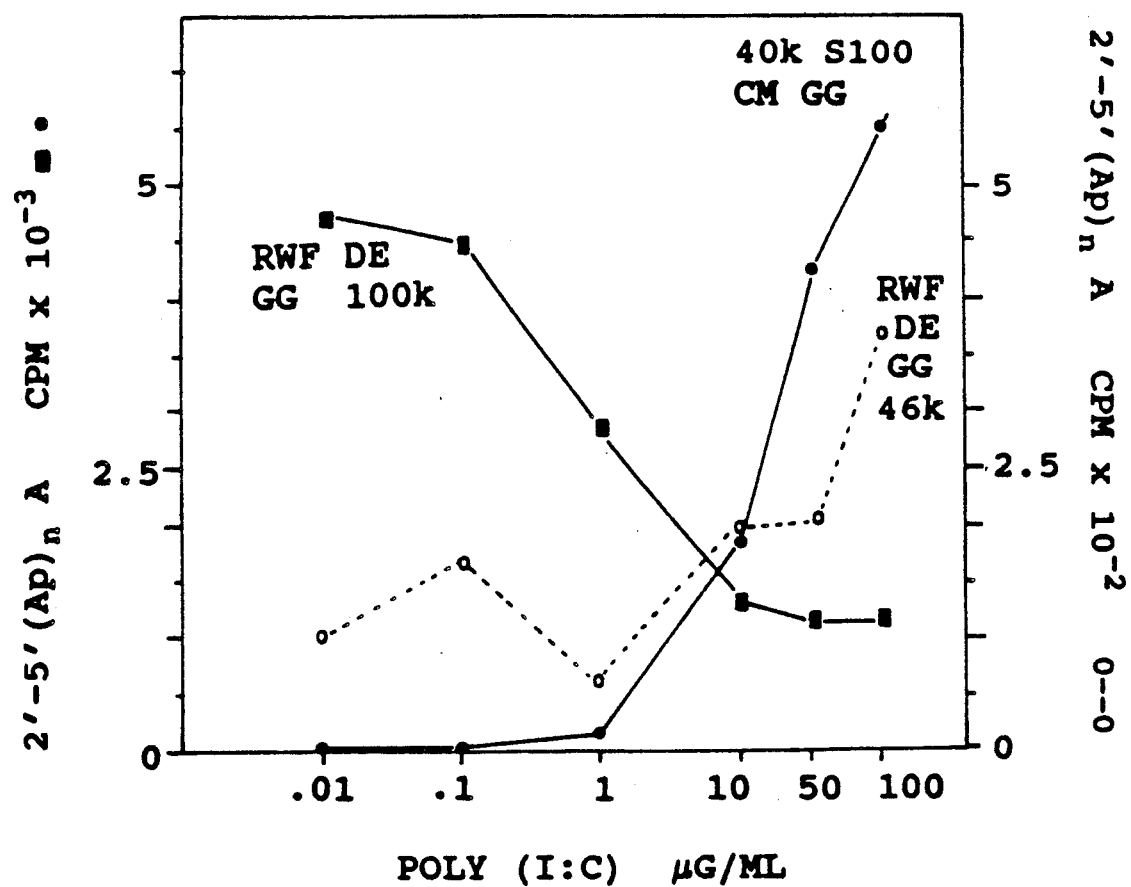
FIG. 20 depicts double stranded RNA requirements of various forms of (2'-5') oligo A synthetase from SV80 cells. Fractions are labeled as in FIG. 19. Enzymatic activity measured at indicated concentrations of poly (rI)(rC).

C) Different enzymatic properties of the various (2'-5') oligo A synthetase form The 40 kd proteins from the glycerol gradient has an optimal pH of 6.8 for its activity, and is only 25% as active at pH 7.8. Moreover, no activity of the 40 kd (2'-5') oligo A synthetase can be observed at concentrations of poly (rI)(rC) lower than 1μg/ml and the maximal activity required 500-100μg/ml (FIG. 20). The same high ds RNA requirement was found for the E16 cDNA product produced by recombinant DNA technology in *E. coli* (not shown).

The 100 kd protein after the glycerol gradient, has an optimal pH of 7.6 for its (2'-5') oligo A synthetase activity and is less active at acidic pH. It is maximally active already at extremely low concentrations of poly (rI)(rC) or in its absence, and its activity is even inhibited by high ds RNA concentrations This strongly suggests that the different (2'-5') oligo A synthetase forms, because of their different cytoplasmic localizations and enzymatic properties, are used by the cells under different conditions.

Many observations suggest that the IFN-induced (2'-5') oligo A synthetase involved in two distinct, seemingly opposite, phase of cell growth (cell-cycling and growth inhibition) in addition to its possible role in the antiviral effect (reviewed in Revel, 1984). This may be relevant to the issue of multiple (2'-5') oligo A synthetase forms. In synchronized cell cultures we have observed that (2'-5') oligo A synthetase behaves as a cell-cycle protein (Mallucci, et al., 1985). Thus, synchronized cultures of Mouse embryo fibroblasts exhibit a sharp rise in (2'-5') oligo A synthetase activity and (2'-5') oligo A synthetase mRNA at the end of the S-phase followed by a rapid disappearance of the RNA and enzyme activity when the cells proceed to G2. Anti-mouse IFN antibodies reduced the (2'-5') oligo A synthetase induction. In this system we also observed that the (2'-5') oligo A synthetase RNA which accumulates in S-phase is a large 4-5 kb transcript different from the 1.7 kb RNA species which accumulated in the same cells when treated with exogenous IFN. This suggests that the S-phase (2'-5') oligo A synthetase is a different form of the enzyme than that in cells growth-arrested by exogenously added IFN. Because of its large mRNA it is likely to be like the 100 kd, a low ds RNA requiring form. Anti-B antibodies also detected the (2'-5') oligo A synthetase multiple forms in mouse cells.

These considerations illustrate the advantage of being able to assay independently the 4 forms of (2'-5') oligo A synthetase, which may vary individually in various physiological conditions and diseases

EXAMPLE 15

Use of anti-(2'-5') oligo A synthetase peptides antibodies for immunoassays of (2'-5') oligo A synthetase Since the anti-B antibodies recognizes all the forms of (2'-5') oligo A synthetase, it can be used for an immunoassay of (2'-5') oligo A synthetase in unfractionated extracts of human cells either from cultures or directly obtained from patients.

Figure 21:
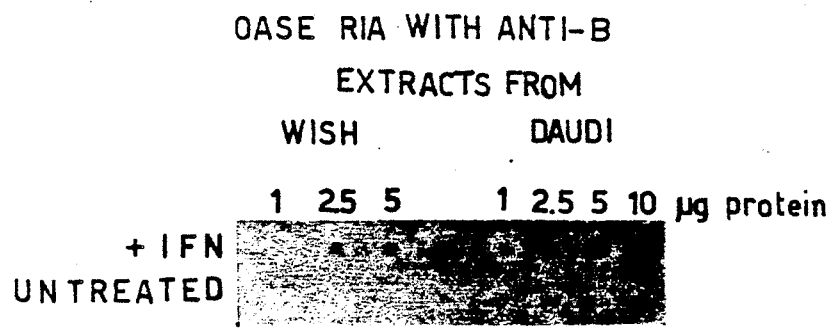
FIG. 21 depicts the results of a radio-immunoassay of (2'-5') oligo A synthetase with anti-B IgG and $^{125}$I-Protein A as described in Example 15. Autoradiography is shown. Cells treated for 16 hours with 500 U/ml IFN-β1 or left untreated.

An example of a solid-phase radio-immunoassay is shown in FIG. 21. Wish and Daudi cells, either treated by IFN or untreated, were lysed by the NP40 containing Buffer A and S15 prepared by microfuge centrifugation as described above. Aliquots containing 1 to 10μg of protein were directly applied to nitrocellulose paper (or to other protein-binding paper) and the sheet treated with anti-B as for regular immunoblots (Example 14). The autoradiography in FIG. 21 shows that $^{125}$I-Protein A binds only to the samples originating from IFN-treated cells. It is clear that this assay may also be used in the form of an enzyme-linked immunoassay (ELISA) by replacing the labeled Protein-A with peroxydase or β-galactosidase conjugated antirabbit IgG.

The immunoassay of (2'-5') oligo A synthetase is rapid: 20 minutes for cell extract preparation; 2 hours for anti-B and Protein-A adsorption and washing. The assay is sensitive and very small amounts of cell extracts suffice to measure the (2'-5') oligo A synthetase level. It is specific, no signal being obtained in non-IFN treated cells.

EXAMPLE 1

Immunofluorescence microscopy detection of (2'-5') oligo A synthetase in cells

Enzymatic assays have established that (2'-5') oligo A synthetase is elevated in peripheral blood mononuclear cells of patients with viral infections. The anti-(2'-5') oligo A synthetase peptide antibodies of the present invention can be used in immunofluorescence microscopy to detect (2'-5') oligo A synthetase elevation in cells in general, and white blood cells in particular.

Blood (2 ml) was withdrawn from a healthy donor and from a patient with acute viral illness. The mononuclear blood cells were separated by Ficoll-Hypaque (Pharmacia) centrifugation, and spread on glass coverslips directly or by the use of a cytospin microfuge (microhematocrite). The cells were washed in PBS, fixed for 30 minutes in 3% paraformaldehyde at room temperature (RT), rinsed with PBS and treated with 0.5% Triton-X 100 in Hank's salts for 5 minutes, rinsed again with PBS and with PBS-2% gelatin. The coverslips were then incubated with anti-B serum diluted 1:5 in PBS-gelatin applied as a 40μl droplet on parafilm onto which the coverslips were deposited. After 60 minutes at RT, the coverslips were rinsed in PBS-gelatin and FITC conjugated anti-rabbit IgG (BioYeda) diluted 1:20 was applied by the parafilm procedure. After 20 minutes at room temperature, coverslips were washed twice with PBS-gelatin, then with H$_2$O and mounted on microscopic slides with Moviol 4–88 (Hoechst)-Glycerol (2.5g Moviol, 6g Glycerol and 6 ml H$_2$O to which 12 ml of 0.2M Tris-HCl, pH 8.5, were added, followed by incubation at 50° C. and clarification 15 minutes at 5,000Y). Parallel coverslips were processed using normal rabbit serum instead of anti-B Slides were observed in a Zeiss fluorescence microscope and photographed on Polaroid film with 30 seconds exposures.

FIG. 22 shows that the lymphocytes were stained with anti-(2'-5') oligo A synthetase in blood samples from the patient with viral infection but not in the blood of the healthy donor, where only a low fluoresence of macrophages and granulocytes is seen. Thus, the present anti-(2'-5') oligo A synthetase peptide antibodies can be used for microscopic observation of cells, in cultures, blood and tissue sections, to evaluate if the cells have reacted with interferon and have accumulated (2'-5') oligo A synthetase.

References

1. Baglioni, C. and Nilsen, T. W. (1983), in Gresser, I.(ed) *Interferon* 5, Acad Press, New York, pp. 23–42.
2. Ball, L. A. (1980), Ann. N.Y. Acad. Sci. 350: 486–496.
3. Benech, P., Merlin, G., Revel, M. and Chebath, J. (1985), Nucl. Acids Res. 13: 1267–1281.
4. Benech, P., Mory Y., Revel, M. and Chebath, J. (1985b), EMBO J. 4:2249–2256.
5. Bradford, M. (1976), Anal. Biochem. 72:248.
6. Breathnach, R. and Chambon, P. (1981), Ann. Rev. Biochem. 50: 349–383.
7. Chebath, J., Merlin, G., Metz, R., Benech, P. and Revel, M. (1983), Nucl. Acids Res. 11: 1213–1226.
8. Chernajovsky, Y., Mory, Y., Chen, L., Marks, Z., Novick, D., Rubinstein, M. and Revel, M. (1984), DNA 3:297–308.
9. Creasey, A., Eppstein, D. A., Marsh, Y. V., Khan, Z. and Merigan, T. C. (1983), Mol Cell. Biol. 3: 780–786.
10. Degrave, W., Derynck, R., Tavernier, J., Haegemen, G. and Fiers, W. (1981), Gene 14: 137–143.
11. Dougherty, J., Samanta, H., Farrell, P. and Lengyel, P. (1980), J. Biol. Chem. 255: 3813–3816.
12. Epstein, D. A., Czarniecki, W., Jacobson, H , Friedman, R. M. and Panet, A. (1981), Eur. J. Biochem. 118: 9–15.
13. Etienne-Smekens, M., Goldstein, J., Ooms, H. and Dumont, J. (1983), Eur. J. Biochem. 130: 269–273.
14. Fellous, M., Nir, U., Wallach, D., Merlin, G., Rubinstein, M. and Revel, M. (1982), Proc. Natl. Acad. Sci. USA 79: 3082–3086.
15. Ferbus, D., Justesen, J., Besancon, F. and Thang, M. N. (1981), Biochem. Biophys. Res. Commun 100:847–856.
16. Friedman, R. L., Manly, S. P., McMahon, M. Kerr, I. M. and Stark, G. R. (1984), Cell 38: 745–755.
17. Green, N., Alexander, H., Olson, A., Alexander, S., Schinnick, T., Sutcliffe, G. and Lerner, R. (1982), Cell 28:477–487.
18. Green, M., Maniatis, T. and Melton, D. A. (1983), Cell 32: 681–694.
19. Hoare, D. and Koshland D. (1967), J. Biol. Chem. 242:2447–2453.
20. Hovanessian, A. G., Brown, R. E. and Kerr, I. M. (1977), Nature 268: 537–540.
21. Johnston, M., Friedman, R. M. and Torrence, P. F. (1980), Biochemistry 19: 5580–5585.
22. Karin, M. and Richards, R. I. (1982), Nature 299: 797–802.
23. Keller, W. (1984), Cell 39: 423–425.
24. Kerr, I. M. and Brown, R. E. (1978), Proc. Natl. Acad. Sci. USA 75: 256–260.
25. Kimchi, A., Shure, H., Lapidot, Y., Rapoport, S., Panet, A. and Revel, M. (1981), FEBS Lett. 134: 26.
Kitamura, N., Semler, B. L., Rothberg, P. G., Larsen, G. R., Adler, C. J., Dorner, A. J., Emini, E. A., Hanecak, R., Lee, J. J., van der Werf, S., Anderson, C. W. and Wimmer, E. (1981), Nature 291: 547–553.
27. Kozak, M. (1984), Nature 308: 241–246.
28. Krishnan, I. and Baglioni, C. (1980), Proc. Natl. Acad. Sci. USA 77: 6506–6510.

29. Kyte, J. and Doolittle, R. F. (1982}, J. Mol. Biol. 157: 105-132.

30. Laemmli, W. K., (1970), Nature 227: 680-685.

31. Laurence, L., Marti, J., Roux, D. and Cailla, H. (1984), Proc. Natl. Acad. Sci. USA 81: 2322-2326.

32. Lebleu, B. and Content, J. (1982) in Gresser, I. (ed) *Interferon* 4, Acad. Press, New York, pp. 47-48.

33. Lengyel, P. (1982), Ann. Rev. Biochem. 51: 251-282.

34. Malissen, M., Malissen, B. and Jordan, B. (1982), Proc. Natl. Acad. Sci. USA 79: 893-897.

35. Mallucci, L., Chebath, J., Revel, M. Wells, V. and Benech, P. (1985), In: Dianzani, F., Rossi, G. B. (eds): "The Interferon System", Serono Symposium Vol. 24, New York, Raven Press, pp. 165-170.

36. Maniatis, T., Hardison, R., Lacy, E., Lauer, J., O'Connell, C., Quon, D., Gek Kee, S. and Efstradiatis, A. (1978}, Cell 15: 687-701.

37. Maniatis, T., Fritsch, P. and Sambrook, J. (1982), *Molecular Clonino: A laboratory manual*, Cold Spring Harbor Laboratory, Cold String Harbor, N.Y.

38. Maxam, A. M. and Gilbert, W. (1980), Meth. Enzymol 65: 499-560.

39. Merlin, G., Chebath, J., Benech, P., Metz, P. and Revel, M. (1983), Proc. Natl. Acad. Sci. USA 80: 4904-4908.

40. Minks, M. A., West, D. K., Benvin, S. and Baglioni, C. (1979), J. Biol. Chem. 254: 10180-10183.

41. Mory, Y., Chernajovsky, Y., Feinstein, S. L., Chen, L., Nir, U., Weissenbach, J., Malpiece, Y., Tiollais, P., Marks, D., Ladner, M., Colby, C. and Revel, M. (1981), Eur. J. Biochem. 120: 192-202.

42. Nilsen, T. M., Maroney, P. A., Robertson, H. D. and Baglioni, C. (1982a), Mol. Cell. Biol. 2: 154-160.

43. Nilsen, T. M., Wood, D. L. and Baglioni, C. (1982b), J. Biol. Chem. 257: 1602-1605.

44. Nir, U., Cohen, B., Chen, L. and Revel, M. (1984), Nucl. Acids. Res. 12: 6979-6993.

45. Pustell, J. and Kafatos, F. C. (1982a), Nucl. Acids Res. 10: 4765-4782.

46. Pustell, J. and Kafatos, F. C. (1982b), Nucl. Acids Res. 10: 51-59.

47. Raj, N. B. K. and Pitha, P. N. (1981), Proc. Natl. Acad. Sci. USA 78: 7426-7430.

48. Revel, M. (1984), in Becker, Y. (ed), *Antiviral Drugs and Interferons: The Molecular basis of their activity*. Martinus Nijhoff, Boston, pp. 357-433.

49. Revel, M., Kimchi, A., Shulman, L. Fradin, A., Shuster, R., Yakobson, E., Chernajovsky, Y., Schmidt, A., Shure, H. and Bendori, R. (1980), Ann. N.Y. Acad. Sci. 350: 459-472.

50. Revel, M., Wallach, D., Merlin, G., Schattner, A., Schmidt, A., Wolf, D., Shulman, L. and Kimchi, A. (1981), Meth. Enzymol. 79: 149-161.

51. Revel, M., Kimchi, A., Friedman, M., Wolf, D., Merlin, G., Panet, A., Rapoport, S. and Lapidot, Y. (1982) Texas Rep. Biol. Med. 41: 452-462.

52. Revel, M. (1984), The Interferon System in Man: Nature of the Interferon Molecules and Mode of Action. In Becker, Y (ed): "Antiviral Drugs and Interferon: The Molecular Basis of Their Activity", Boston: Martinus Nijhoff Publishing, pp. 357-433.

53. Rigby, P. Dieckman, M., Rhodes, C. and Berg, P. (1977), J. Mol. Biol. 113: 237-251.

54. Rosa, F., Berissi, H., Weissenbach, J., Maroteaux, L., Fellous, M. and Revel, M. (1983a), EMBO J. 2: 55. Rosa, F., Hatat, D., Adadie, A., Wallach, D., Revel, M. and Fellous, M. (1983b), EMBO J. 2, 585-1589.

56. Salzberg, S., Wreschner, D. H., Oberman, F., Panet, A. and Bakhanaschvili, M. (1983), Mol. Cell. Biol. 3, 1759-1765.

57. Samanta, H., Dougherty, J. P. and Lengyel, P. (1980), J. Biol. Chem. 255: 9807-9813.

58. Samanta, H., Pravtcheva, D. D., Ruddle, F. H. and Lengyel, P. (1984), J. Interferon Res. 4, 295-300.

59. Saunders, M. E. and Williams, B. R. G. (1984), Antiviral Res. ABSTR No. 3, p. 60.

60. Schamboeck, A., Korman, A. J., Kamb, A. and Strominger, J. L. (1983}, Nucl. Acids Res. 11: 8663-8675.

61. Schattner, A., Wallach, D., Merlin, G., Hahn, T., Levin, S. and Revel, M. (1981), Lancet ii: 497-500.

62. Schmidt, A., Zilberstein, A., Shulman, L., Federman, P., Berissi, H. and Revel, M. (1978), FEBS Lett. 25: 257-264.

63. Spirer, Z., Zakut, R. Bogair, N. and Fridkin, M. (1977), Eur. J. Immunol. 7, 69-74.

64. Shulman, L. M. Barker, P. E., Hart, J. T., Messer Peter, P. G. and Ruddle, F. H. (1984), Somatic Cell Mol. Genet. 10: 247-257.

65. Shulman, L. and Revel, M. (1980), Nature 287: 98-100.

67. Stark, G., Dower, W. J., Schimke, R. T., Brown, R. E. and Kerr, I. M. (1979) Nature 278: 471-473.

67. St. Laurent, G., Yoshie, O., Floyd-Smith, G., Samanta, H., Sehgal, P. and Lengyel, P. (1983), Cell 33, 95-102.

68. Strachan, T., Sodoyer, R. Damotte, M. and Jordan, B. R. (1984), EMBO J. 3: 887-894.

69. Thomas (1980), Proc. Natl. Acad. Sci. USA 77: 201-5205.

70. Trifonov, E. N. (1984), Codata Bulletin 56: 21-26.

71. Wallach, D. and Revel, M. (1980), Nature 287: 68-70.

72. Wallach, D., Fellous, M. and Revel, M. (1982), Nature 299: 833-836.

73. Wallach, D., Schattner, A., Merlin, G., Kimchi, A., Fellous, M. and Revel, M. (1982), in Meringan, T. C., Friedman, R. M. (eds) Interferons, UCLA Symposia Vol. XXV, Acad. Press. New York, pp. 449-463.

74. Wallach, D., Aderka, D., Budilovsky, S. and Hahn, T. (1983), in DeMaeyer, E., Schellekens, H. (eds) *The Biology of the Interferon System*, Elsevier Sci. Publ., Amsterdam, pp. 293-303.

75. Weil, J., Epstein, C. J., Epstein, L. B., Sednak, J. J, Sabran, J. L., Grossberg, S. E. (1983), Nature 301: 437-439.

76. Weissenbach, J., Zeevi, M., Landau, T. and Revel, M. (1979), Eur. J. Biochem 98: 1-8.

77. Wells, V. and Mallucci, L. (1985), J. Cell Biol., in press.

78. Wigler, M., Sweet, R., Sim, G. K., Wold, B., Pellicer, A., Lacy, E., Maniatis, T., Silverstein, S. and Axel, R. (1979), Cell 16: 777-785.

79. Wolf, D. and Rotter, V. (1985), Proc. Natl. Acad. Sci. USA 82: 790-794.

80. Yang, K., Samanta, H., Dougherty, J., Jayaram, B., Broeze, R. and Lengyel, P. (1981), J. Biol. Chem. 256: 9324-9328.

81. Yarden, A., Shure-Gottlieb, H., Chebath, J., Revel, M. and Kimchi, A. (1984), EMBO J. 3, 969-973.

82. Zilberstein, A., Kimchi, A., Schmidt, A. and Revel, M. (1978), Proc. Natl. Acad. Sci. USA 75: 4734-4738.

83. Zinn, K., DiMaio, D. and Maniatis, T. (1983), Cell 34: 865-879.

What is claimed is:

1. An antibody against all four of the 40 kd, 46 kd, 67 kd, and 100 kd forms of human (2'-5') oligo A synthetase obtained by immunizing an animal with an antigenic peptide having an amino acid sequence consisting of GLU-LYS-TYR-LEU-ARG-ARG-GLN-LEU-THR-LYS-PRO-ARG-PRO-VAL-ILE-LEU-ASP-PRO-ALA-ASP.

2. A antibody of claim 11 conjugated with a label to formed a labeled antibody.

3. A labeled antibody of claim 2, wherein the label is a fluorescent label.

4. A labeled antibody of claim 2, wherein the label is a radioactive label.

5. A labeled antibody of claim 2, wherein the label is an enzyme.

6. A kit for the detection of all four forms of human (2'-5') oligo A synthetase in cells comprising the antibody of claim 2.

7. An antibody which specifically recognizes and binds to human (2'-5') oligo A synthetase and an antigenic peptide having an amino acid sequence contained within the amino acid sequence set forth in FIG. 7A comprising consisting of ARG-PRO-PRO-ALA-SER-SER-LEU-PRO-PHE-ILE-PRO-ALA-PRO-LEU-HIS-GLU-ALA.

8. An antibody which specifically recognizes and binds to human (2'-5') oligo A synthetase and an antigenic peptide having an amino acid sequence contained within the sequence of amino acid 1–364 set forth in FIG. 7A consisting of GLU-LYS-TYR-LEU-ARG-ARG-GLN-LEU-THR-LYS-PRO-ARG-PRO-VAL-ILE-LEU-ASP-PRO-ALA-ASP.

* * * * *